US006747188B2

(12) United States Patent
Hanley-Bowdoin et al.

(10) Patent No.: US 6,747,188 B2
(45) Date of Patent: Jun. 8, 2004

(54) GEMINIVIRUS RESISTANT TRANSGENIC PLANTS EXPRESSING A MUTANT GEMINIVIRUS AL3/C3 CODING SEQUENCE

(75) Inventors: Linda Hanley-Bowdoin, Raleigh, NC (US); Sharon Settlage, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 129 days.

(21) Appl. No.: 09/164,615

(22) Filed: Oct. 1, 1998

(65) Prior Publication Data

US 2002/0073442 A1 Jun. 13, 2002

(51) Int. Cl.[7] ........................ C12N 15/33; C12N 15/82; C12N 15/84; A01H 5/00; A01H 5/10

(52) U.S. Cl. .................... 800/280; 435/320.1; 435/468; 536/23.72; 800/293; 800/294; 800/298; 800/317; 800/317.4

(58) Field of Search ............................. 435/69.1, 320.1, 435/410, 411, 417, 419, 468, 469, 470; 536/24.1, 23.72; 800/278, 279, 280, 288, 292, 293, 294, 295, 298, 301, 317, 317.4

(56) References Cited

U.S. PATENT DOCUMENTS

| | | | |
|---|---|---|---|
| 5,589,367 A | 12/1996 | Donson et al. | 435/468 |
| 5,589,379 A | 12/1996 | Kridl et al. | 435/320.1 |
| 5,650,303 A | 7/1997 | Kridl et al. | 435/91.41 |
| 5,850,023 A | 12/1998 | Elmer et al. | 800/280 |

FOREIGN PATENT DOCUMENTS

| | | | |
|---|---|---|---|
| WO | WO 95/03404 | 2/1995 | C12N/15/11 |
| WO | WO/96/08573 | 3/1996 | C12N/15/82 |
| WO | WO 97/39110 | 10/1997 | C12N/5/14 |
| WO | WO 97/42315 | 11/1997 | C12N/15/10 |
| WO | WO97/42315 | 11/1997 | C12N/15/10 |
| WO | WO 97/42316 | 11/1997 | C12N/15/10 |

OTHER PUBLICATIONS

Hormuzdi et al, Virology, vol. 206, pp. 1044–1054, 1995.*

Estammi et al, J. Gen. Virology, vol. 72, pp. 1005–1012, 1991.*

Morris et al, J. Gen. Virol., vol. 72, pp. 1205–1213, 1991.*

McCormick et al, Plant Cell Rep., vol. 5, pp. 81–84, 1986.*

Sunter et al, Virology, vol. 195, pp. 275–280, 1993.*

Sung et al, J. Gen. Virol, vol. 76, pp. 1773–1780, 1995.*

Hanley–Bowdoin et al., "Functional Expression of the Leftward Open Reading Frames of the A Component of Tomato Golden Mosaic Virus in Transgenic Tobacco Plants," *The Plant Cell*, 1:1057–1067 (Nov. 1989).

Pedersen et al., "Molecular Characterization of the AL3 Protein Encoded by a Bipartite Geminivirus," *Virology*, 202:1070–1075 (1994).

Bendahmane et al; *Engineering resistance against tomato yellow leaf curl virus (TYLCV) using antisense RNA, Plant Molecular Biology*, 33:351–357 (1997).

Eagle et al.; *A DNA Sequence Required for Geminivirus Replication Also Mediates Transcriptional Regulation, The Plant Cell*, 6:1157–1170 (Aug. 1994).

Fontes et al.; *A Geminivirus Replication Protein Is a Sequence–Specific DNA Binding Protein, The Plant Cell*, 4:597–608 (May 1992).

Orozco et al; *A DNA Structure Is Required for Geminivirus Replication Origin Function, Journal of Virology*, 70:148–158 (Jan. 1996).

Orozco et al.; *Functional Domains of a Geminivirus Replication Protein, Journal of Biological Chemistry*, 272:9840–9846 (1997).

Pedersen et al.; *Molecular Characterization of the AL3 Protein Encoded by a Bipartite Geminivirus, Virology*, 202:1070–1075 (1994).

Settlage et al.; *Interactions between Geminivirus Replication Protein, Journal of Virology*, 70:6790–6795 (Oct. 1996).

* cited by examiner

*Primary Examiner*—Ashwin Mehta
(74) *Attorney, Agent, or Firm*—Myers Bigel Sibley & Sajovec, P.A.

(57) ABSTRACT

Transgenic plants with increased resistance to geminivirus infection, and nucleic acid constructs useful in producing such plants, are described. The transgenic plants express a mutant AL3/C3 geminivirus protein, which increases resistance to infection by at least one geminivirus, compared to a non-transformed control plant.

19 Claims, 11 Drawing Sheets

FIG. 3A

| SEQ. ID No. | | | | | | | |
|---|---|---|---|---|---|---|---|
| 1 | Consensus | 1 | MVMDSRTGEL | ITAHQAENGV | YIWEIxNPLY | FKITRVEDPP | YTRTRIYHTx |
| 2 | TYCLV-DR | 1 | M--DSRTGEL | ITAPQAENGV | FIWEINNPLY | FKITDHSQRP | FLMNHDIISI |
| 3 | TYLCV-IS | 1 | M--DLRTGEY | ITAHQATSGV | YTFGITNPLY | FTITRHNQNP | FNNKYNTLTF |
| 4 | ICMV | 1 | M--DSRTGEL | ITAAQAMNGV | FIWEVPNPLY | FKIIQHDNRP | FVMNQDIITV |
| 5 | TYLCU | 1 | M--DLRTGEY | ITAHQATSGV | YTFEITNPLY | FTITRHNQQP | FNSKYNFLTF |
| 6 | TYLCA | 1 | M--DSRTGEP | ITARQAMNGE | YIWRVPNPLY | FKIIKHHKRP | FNYNHDIIQV |
| 7 | TYLCM | 1 | M--DLRTGEY | ITAHQATSGV | YTFGITNPLY | FTITRHNQNP | FNNKYNTLTF |
| 8 | ACMV | 1 | M--DLRTGEL | ITAPQAMNGV | YTWEINNPLY | FTITRHQQRP | FLLNQDIITV |
| 9 | AbMV | 1 | M--DSRTGEF | ITVHQAENGV | YIWEIANPLY | FRIYKVEDPL | YTRTRIYHV- |
| 10 | BDMV | 1 | M--DSRTGEL | ITALQAENGV | YIWEIENPLY | FKIYRVEEPL | YTNSRVYSV- |
| 11 | BGMV | 1 | M--DSRTGEN | ITAHQAENSV | FIWEVPNPLY | FKIMRVEDPA | YTRTRIYHI- |
| 12 | BGMV-BZ | 1 | --MDSRTGER | ITARQAENGV | YIWEISNPLY | FKMYNVEDLQ | YTTTRVYHL- |
| 13 | PHV | 1 | --MDLRTGVP | ITAAQAANGV | FIWELRNPLY | FKIRLVETPM | YTRSRVFHI- |
| 14 | PYMV | 1 | M--DSRTGEL | ITARQAENGV | FIWEIENPLY | FKINQVEDMQ | YTRTRIYSV- |
| 15 | SqLCV | 1 | MVMDLRTWDD | ITVHQAENSV | FIWEVPNPLY | FKMYXVEDPL | YTHTRIYHI- |
| 16 | TGMV | 1 | M--DSRTGEP | ITVPQAENGV | YIWEITNPLY | FKIISVEDPL | YTNTRIYHL- |
| 17 | ToMoV | 1 | M--DSRTGEL | ITAHQAENGV | YIWELENPLY | FKIHRVEDPL | YTRTRVYHV- |

| | | | | | | |
|---|---|---|---|---|---|---|
| Consensus | 51 | QIRFNHNLRK | ALGLHKAFLN | FQVWTTxQTA | SGxTYLxRFx | YLVLKYLDNL |
| TYCLV-DR | 49 | QIRFNHNIRK | VMGIHKCFLN | FRIWTTL--Q | TGR-FLRVFR | YGVLKYLDSL |
| TYLCV-IS | 49 | QIRFNHNLRK | ELGIHKCFLN | FHIWTTLQSP | TGH-FLRVFK | YQVCKYLNNL |
| ICMV | 49 | QIRFNHNLRK | ALGLHQCWMD | FKVWTTLQPQ | TWR-FLRVFK | TQVLKYLDSL |
| TYLCU | 49 | QIRFNHNLRK | ALGIHKCFLN | FRIWTTLQSP | TGH-FLRVFR | YQVYKYLNNI |
| TYLCA | 49 | RIQFNHNLRR | ALAIHKCFLD | FTVFTRLQPA | TWR-FLRVFK | TQVMKYLDSL |
| TYLCM | 49 | QIRFNHNLRK | ELGIHKCFLN | FHIWTTLQSP | TGH-FLRVFK | YQVCKYLNNL |
| ACMV | 49 | QVRFNHNLRK | ELGIHKCFLN | FRIWTTLRPQ | TGL-FLRVFR | YQVLKYLDNI |
| AbMV | 48 | QIRFNHNLRR | ALHLHKAYLN | FQVWTTSMTA | SGSIYLNRFR | RLVNMYLDQL |
| BDMV | 48 | QIRFNHNLRR | ALHLHKAFLN | FQVWTISTTA | SGSTYLNRFK | HLVIMYLDQL |
| BGMV | 48 | QIRFNHNLRK | ALDLHKAFLN | FQVWTTSIQA | SGTTYLNRFR | LLVLLYLHRL |
| BGMV-BZ | 48 | QIRFNHNLRN | KLGLHKAFLN | FQVWTISLQA | SGTTYLNRFK | YLVLLYLDRI |
| PHV | 48 | QVRANHNMRT | ALGLHKAYFN | FQVWTTLTTI | SGQIYLNRFK | LLVMFYLDNL |
| PYMV | 48 | QIRFNHNLRR | ALDLHKAYLN | FQVWTTSMTA | SGSNYLARFR | QLVLLYLDRL |
| SqLCV | 50 | QIRFNHNLRR | ALNLHKAFLN | FQVWTESIRA | SGTTYLNRFR | HLVMLYLDRL |
| TGMV | 48 | QIRFNHNLRR | ALDLHKAFLN | FQVWTTSTTA | SGRTYLNRFK | YLVMLYLEQL |
| ToMoV | 48 | QIRFNHNLRK | ALHLHKAYLN | FQVWTTSMTA | SGSIYLARFR | YLVNMYLDQL |

FIG. 3B

| | | | | | |
|---|---|---|---|---|---|
| Consensus | 101 | GVISINNVIR | AVxFATFDVS | YVTIDYLENH | EIKFKFY |
| TYCLV-DR | 96 | GVISINNVIR | AVDHVLYDVL | ENTINVTETH | DIKYKFY |
| TYLCV-IS | 98 | GVISLNNVVR | AVDYVLFHVF | ERTIDVTENH | EIKFNFY |
| ICMV | 98 | GVISINTIVK | AVEHVLYNVI | HGTDRVEQSN | LIKLNIY |
| TYLCU | 98 | GIVSLNNVIR | AVDYVLFDVF | ENTIDVIEQH | EIKYNLY |
| TYLCA | 98 | GVISINNVIR | SVDHVLYNVL | DSTFDVIEDH | DIKFNFY |
| TYLCM | 98 | GVISLNNVVR | AVDYVLFHVF | ERTIDVTENH | EIKFNFY |
| ACMV | 98 | GVISINDVIR | AACHVLFNVI | EKTIECQLTH | EIKFNVY |
| AbMV | 98 | GVISINNVIR | AVQFAT-NRT | YVNY-VLENH | SIKFKFY |
| BDMV | 98 | GIISINNVIR | GVRFAT-DRS | YVTH-VIEYH | SIKFKLY |
| BGMV | 98 | GVIGINNVIR | AVQFAT-NKS | YVNT-VLENH | DIKYKFY |
| BGMV-BZ | 98 | GVISLNNVIR | AVRFAT-DKS | YVNY-VLENH | EIKYKFY |
| PHV | 98 | GLISVNNVIR | AVSFAT-DKR | YVNA-VLENH | EIIYKLY |
| PYMV | 98 | GVISINNVIR | SVRFAT-DRS | YVNY-VLENH | SIKYKFY |
| SqLCV | 100 | GVIGLNNVIR | AVSWAT-DRS | YVNY-VLENH | EIKFKIY |
| TGMV | 98 | GVICINNVIR | AVRFAT-DRS | YITH-VLENH | SIKYKFY |
| ToMoV | 98 | GVISINNVVR | AVRFAT-NRV | YVNH-VLENH | SIKFKFY |

| | 10 | 20 | 30 | 40 | 50 | 60 | 70 | 80 |
|---|---|---|---|---|---|---|---|---|
| TYLCV-DR | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #15 | MASATGELIT | APQAENGVFI | WEINNPLYFK | ITDHSQRPFL | MNHDIISIQI | RFNHNIRKVM | GIHKCFLNFR | IWTTQTGRFL |
| Mutant #17 | MDSRTGELIT | APQAENGVFI | WEINNPLAAA | ITDHSQRPFL | MNHDIISIQI | RFNHNIRKVM | GIHKCFLNFR | IWTTQTGRFL |
| Mutant #19 | MDSRTGELIT | APQAENGVFI | WEINNPLYFK | ITDHSQRPFL | MNHDIISIQI | RFNHNIAAVM | GIHKCFLNFR | IWTTQTGRFL |
| Mutant #21 | MDSRTGELIT | APQAENGVFI | WEINNPLYFK | ITDHSQRPFL | MNHDIISIQI | RFNHNIRKVM | GIHKCFLNFR | IAATQTGRFL |
| Mutant #23 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #25 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #27 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #29 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #31 | MDSRTGELIT | APQAENGVFI | WEINNPLYFK | ITDHSQRPFL | MNHDIISIQI | RFNHNIRKVM | GIHKCFLNFR | IAATQTGRFL |
| Mutant #33 | MDSRTGALIA | APAAENGVFI | WEINNPLYFK | ITDHSQRPFL | MNHDIISIQI | RFNHNIRKVM | GIHKCFLNFR | IWTTQTGRFL |
| Mutant #35 | MDSRTGELIT | APQAENGVAI | AEINNPLYFK | ITDHSQRPFL | MNHDIISIQI | RFNHNIRKVM | GIHKCFLNFR | IWTTQTGRFL |
| Mutant #37 | MDSRTGELIT | APQAENGVFI | WEINNPLYFK | ITDHSQAAAL | MNHDIISIQI | RFNHNIRKVM | GIHKCFLNFR | IWTTQTGRFL |
| Mutant #39 | MDSRTGELIT | APQAENGVFI | WEINNPLYFK | ITDHSQRPFL | MNHDIISIAI | AANHNIRKVM | GIHKCFLNFR | IWTTQTGRFL |
| ⋮ | | | | ⋮ | | | | • |

| | | | | | | | | |
|---|---|---|---|---|---|---|---|---|
| Mutant #41 | MDSRTGELIT | APQAENGVFI | WEINNPLYFK | ITDHSQRPFL | MNHDIISIQI | RFAAAIRKVM | GIHKCFLNFR | IWTTQTGRFL |
| Mutant #43 | MDSRTGELIT | APQAENGVFI | WEINNPLYFK | ITDHSQRPFL | MNHDIISIQI | RFNHNIRKVM | GIAACFLNFR | IWTTQTGRFL |
| Mutant #45 | MDSRTGELIT | APQAENGVFI | WEINNPLYFK | ITDHSQRPFL | MNHDIISIQI | RFNHNIRKVM | GIHKCALAAR | IWTTQTGRFL |
| Mutant #47 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #49 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #51 | MDSETGELIT | APQAENGVFI | WEINNPLYFK | ITDHSQRPFL | MNHDIISIQI | RFNHNIRKVM | GIHKCFLNFR | IWTTQTGRFL |
| Mutant #53 | MDSRTGKLIT | APQAENGVFI | WEINNPLYFK | ITDHSQRPFL | MNHDIISIQI | RFNHNIRKVM | GIHKCFLNFR | IWTTQTGRFL |
| Mutant #55 | MDSRTGELIT | APQAENGVFI | WEINNPLYFK | ITDHSQRPFL | MNHDIISIQI | EFNHNIRKVM | GIHKCFLNFR | IWTTQTGRFL |
| Mutant #57 | MDSRTGELIT | APQAENGVFI | WEINNPLYFK | ITDHSQRPFL | MNHDIISIQI | RFNHNIEKVM | GIHKCFLNFR | IWTTQTGRFL |
| Mutant #59 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #61 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #63 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #65 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #67 | MDSRTGELIT | APQAENGVFI | WEINNPLYFK | ITDHSQRPFL | MNHDIISIAA | AAAAAIRKVM | GIHKCFLNFR | IWTTQTGRFL |
| Mutant #69 | MDSRTGELIT | APQAENGVFI | WEINNPLYFK | ITDHSQRPFL | MNHDIISIQI | RFNHNIRKVM | GIHKCALAAR | IAATQTGRFL |
| Mutant #71 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #73 | MDSRTGELIT | APQAENGVFI | WEINNPLYFK | ITDHSQRPFL | MNHDIISIQI | RFNHNIRKVM | GIHKCFLNFR | IWTTQTGRFL |
| Mutant #75 | MDSRTGELIT | APQAENGVFI | WEINNPLYFK | ITDHSQRPFL | MNHDIISIQI | RFNHNIEEVM | GIHKCFLNFR | IWTTQTGRFL |

| | | 100 | 110 | 120 | 130 | | |
|---|---|---|---|---|---|---|---|
| TYLCV-DR | RVFRYGVLKY | LDSLGVISIN | NVIRAVDHVL | YDVLENTINV | TETHDIKYKF | Y | (SEQ ID NO: 2) |
| Mutant #15 | RVFRYGVLKY | LDSLGVISIN | NVIRAVDHVL | YDVLENTINV | TETHDIKYKF | Y | (SEQ ID NO: 18) |
| Mutant #17 | RVFRYGVLKY | LDSLGVISIN | NVIRAVDHVL | YDVLENTINV | TETHDIKYKF | Y | (SEQ ID NO: 19) |
| Mutant #19 | RVFRYGVLKY | LDSLGVISIN | NVIRAVDHVL | YDVLENTINV | TETHDIKYKF | Y | (SEQ ID NO: 20) |
| Mutant #21 | RVFRYGVLKY | LDSLGVISIN | NVIRAVDHVL | YDVLENTINV | TETHDIKYKF | Y | (SEQ ID NO: 21) |
| Mutant #23 | RVAAYGVLKY | LDSLGVISIN | NVIRAVDHVL | YDVLENTINV | TETHDIKYKF | Y | (SEQ ID NO: 22) |
| Mutant #25 | RVFRYGVLKY | LDSLGVISIA | AVIRAVDHVL | YDVLENTINV | TETHDIKYKF | Y | (SEQ ID NO: 23) |
| Mutant #27 | RVFRYGVLKY | LDSLGVISIN | NVIRAVDHVL | YDVLENTINV | TETHDIAYKF | Y | (SEQ ID NO: 24) |
| Mutant #29 | RVFRYGVLKY | LDSLGVISIN | NVIRAVDHVL | YDVLENTINV | TETHDIKAAF | A | (SEQ ID NO: 25) |
| Mutant #31 | RVFAYGVLKY | LDSLGVISIN | NVIRAVDHVL | YDVLENTINV | TETHDIKYKF | Y | (SEQ ID NO: 26) |
| Mutant #33 | RVFRYGVLKY | LDSLGVISIN | NVIRAVDHVL | YDVLENTINV | TETHDIKYKF | Y | (SEQ ID NO: 27) |
| Mutant #35 | RVFRYGVLKY | LDSLGVISIN | NVIRAVDHVL | YDVLENTINV | TETHDIKYKF | Y | (SEQ ID NO: 28) |
| Mutant #37 | RVFRYGVLKY | LDSLGVISIN | NVIRAVDHVL | YDVLENTINV | TETHDIKYKF | Y | (SEQ ID NO: 29) |
| Mutant #39 | RVFRYGVLKY | LDSLGVISIN | NVIRAVDHVL | YDVLENTINV | TETHDIKYKF | Y | (SEQ ID NO: 30) |
| • • • | | | | | | | • • • |

| | | | | | | | |
|---|---|---|---|---|---|---|---|
| Mutant #41 | RVFRYGVLKY | LDSLGVISIN | NVIRAVDHVL | YDVLENTINV | TETHDIKYKF | Y | (SEQ ID NO: 31) |
| Mutant #43 | RVFRYGVLKY | LDSLGVISIN | NVIRAVDHVL | YDVLENTINV | TETHDIKYKF | Y | (SEQ ID NO: 32) |
| Mutant #45 | RVFRYGVLKY | LDSLGVISIN | NVIRAVDHVL | YDVLENTINV | TETHDIKYKF | Y | (SEQ ID NO: 33) |
| Mutant #47 | RVFRYGVLAA | LASLGVISIN | NVIRAVDHVL | YDVLENTINV | TETHDIKYKF | Y | (SEQ ID NO: 34) |
| Mutant #49 | RVFRYGVLKY | LDSLGVISIN | NVIRAVDHVL | YDVLENTINV | TAAAAIKYKF | Y | (SEQ ID NO: 35) |
| Mutant #51 | RVFRYGVLKY | LDSLGVISIN | NVIRAVDHVL | YDVLENTINV | TETHDIKYKF | Y | (SEQ ID NO: 36) |
| Mutant #53 | RVFRYGVLKY | LDSLGVISIN | NVIRAVDHVL | YDVLENTINV | TETHDIKYKF | Y | (SEQ ID NO: 37) |
| Mutant #55 | RVFRYGVLKY | LDSLGVISIN | NVIRAVDHVL | YDVLENTINV | TETHDIKYKF | Y | (SEQ ID NO: 38) |
| Mutant #57 | RVFRYGVLKY | LDSLGVISIN | NVIRAVDHVL | YDVLENTINV | TETHDIKYKF | Y | (SEQ ID NO: 39) |
| Mutant #59 | EVFRYGVLKY | LDSLGVISIN | NVIRAVDHVL | YDVLENTINV | TETHDIKYKF | Y | (SEQ ID NO: 40) |
| Mutant #61 | RVFRYGVLKY | LDSLGVISIN | NVIEAVDHVL | YDVLENTINV | TETHDIKYKF | Y | (SEQ ID NO: 41) |
| Mutant #63 | RVFRYGVLKY | LDSLGVISIN | NVIRAVDHVL | YDVLENTINV | TETHKIKYKF | Y | (SEQ ID NO: 42) |
| Mutant #65 | RVFRYGVLKY | LDSLGVISIN | NVIRAVDHVL | YDVLENTINV | TETHDIEYKF | Y | (SEQ ID NO: 43) |
| Mutant #67 | RVFRYGVLKY | LDSLGVISIN | NVIRAVDHVL | YDVLENTINV | TETHDIKYKF | Y | (SEQ ID NO: 44) |
| Mutant #69 | RVFRYGVLKY | LDSLGVISIN | NVIRAVDHVL | YDVLENTINV | TETHDIKYKF | Y | (SEQ ID NO: 45) |
| Mutant #71 | AAAAYGVLKY | LDSLGVISIN | NVIRAVDHVL | YDVLENTINV | TETHDIKYKF | Y | (SEQ ID NO: 46) |
| Mutant #73 | RVFRYGAAAA | AASLGVISIN | NVIRAVDHVL | YDVLENTINV | TETHDIKYKF | Y | (SEQ ID NO: 47) |
| Mutant #75 | RVFRYGVLKY | LDSLGVISIN | NVIRAVDHVL | YDVLENTINV | TETHDIKYKF | Y | (SEQ ID NO: 48) |

| | 10 | 20 | 30 | 40 | 50 |
|---|---|---|---|---|---|
| TGMV AL3 | MDSRTGEPIT | VPQAENGVYI | WEITNPLYFK | IISVEDPLYT | NTRIYHLQIR |
| mAL3 #17 | MDSRTGEPIT | VPQAENGVYI | WEITNPLAAA | IISVEDPLYT | NTRIYHLQIR |
| mAL3 #67 | MDSRTGEPIT | VPQAENGVYI | WEITNPLYFK | IISVEDPLYT | NTRIYHLAAA |
| mAL3 #69 | MDSRTGEPIT | VPQAENGVYI | WEITNPLYFK | IISVEDPLYT | NTRIYHLQIR |
| mAL3 #71 | MDSRTGEPIT | VPQAENGVYI | WEITNPLYFK | IISVEDPLYT | NTRIYHLQIR |
| mAL3 #73 | MDSRTGEPIT | VPQAENGVYI | WEITNPLYFK | IISVEDPLYT | NTRIYHLQIR |
| mAL3 #75 | MDSRTGEPIT | VPQAENGVYI | WEITNPLYFK | IISVEDPLYT | NTRIYHLQIR |

FIG. 5B

| | 60 | 70 | 80 | 90 | 100 |
|---|---|---|---|---|---|
| TGMV AL3 | FNHNLRRALD | LHKAFLNFQV | WTTSTTASGR | TYLNRFKYLV | MLYLEQLGVI |
| mAL3 #17 | FNHNLRRALD | LHKAFLNFQV | WTTSTTASGR | TYLNRFKYLV | MLYLEQLGVI |
| mAL3 #67 | AAAALRRALD | LHKAFLNFQV | WTTSTTASGR | TYLNRFKYLV | MLYLEQLGVI |
| mAL3 #69 | FNHNLRRALD | LHKAALAAQV | AATSTTASGR | TYLNRFKYLV | MLYLEQLGVI |
| mAL3 #71 | FNHNLRRALD | LHKAFLNFQV | WTTSTTASGR | TYLAAAAYLV | MLYLEQLGVI |
| mAL3 #73 | FNHNLRRALD | LHKAFLNFQV | WTTSTTASGR | TYLNRFKYLA | AAAAAQLGVI |
| mAL3 #75 | FNHNLEEALD | LHKAFLNFQV | WTTSTTASGR | TYLNRFKYLV | MLYLEQLGVI |

FIG. 5C

| | | | | | |
|---|---|---|---|---|---|
| | 110 | 120 | 130 | | |
| TGMV AL3 | CINNVIRAVR | FATDRSYITH | VLENHSIKYK | FY | (SEQ ID NO: 16) |
| mAL3 #17 | CINNVIRAVR | FATDRSYITH | VLENHSIKYK | FY | (SEQ ID NO: 54) |
| mAL3 #67 | CINNVIRAVR | FATDRSYITH | VLENHSIKYK | FY | (SEQ ID NO: 49) |
| mAL3 #69 | CINNVIRAVR | FATDRSYITH | VLENHSIKYK | FY | (SEQ ID NO: 50) |
| mAL3 #71 | CINNVIRAVR | FATDRSYITH | VLENHSIKYK | FY | (SEQ ID NO: 51) |
| mAL3 #73 | CINNVIRAVR | FATDRSYITH | VLENHSIKYK | FY | (SEQ ID NO: 52) |
| mAL3 #75 | CINNVIRAVR | FATDRSYITH | VLENHSIKYK | FY | (SEQ ID NO: 53) |

GEMINIVIRUS RESISTANT TRANSGENIC PLANTS EXPRESSING A MUTANT GEMINIVIRUS AL3/C3 CODING SEQUENCE

FIELD OF THE INVENTION

The present invention relates to transgenic plants with increased resistance to geminivirus infection, and the nucleic acid constructs useful in producing such plants. The transgenic plants express a mutant AL3/C3 geminivirus protein, which increases resistance to infection by geminiviruses.

BACKGROUND OF THE INVENTION

The geminiviruses are a large and diverse family of plant DNA viruses, with circular single-stranded (ss) DNA genomes that replicate through circular double stranded DNA intermediates. See Lazarowitz, *Crit. Rev. Plant Sci.* 11:327 (1992); Timmermans et al., *Annu. Rev. Plant Physiol.* 45:79 (1994). Viral DNA replication, which results in both single and double stranded viral DNAs in large amounts, involves the expression of only a small number of viral proteins that are involved in either replication or viral transcription. The geminiviruses appear to rely primarily on the machinery of the host to copy their genomes and express their genes, including the nuclear DNA and RNA polymerases of their plant hosts. These properties of geminiviruses are unusual among plant viruses, most of which are RNA viruses or replicate through RNA intermediates using virus-encoded replicases. Geminiviruses infect a broad variety of plants and cause significant crop losses worldwide.

Geminiviruses are subdivided on the basis of host range in either monocots or dicots, genome structure, and insect vector. Subgroup I geminiviruses (also known as Mastreviruses) are transmitted by leafhoppers and infect primarily monocots, although Subgroup I geminiviruses that infect dicots are known. Subgroup II geminiviruses (also known as Curtoviruses) are transmitted by leafhoppers and infect dicots. Subgroup III geminiviruses (also known as Begomoviruses) are transmitted by whiteflys and infect dicots. Subgroups I & II viruses have genomes comprising a single ssDNA component; Subgroup III geminiviruses typically have a bipartite genome comprising two similarly sized DNAs (usually termed A and B), as illustrated by African cassava mosaic virus (ACMV), tomato golden mosaic virus (TGMV) and potato yellow mosaic virus. However, monopartite geminiviruses that infect dicots are known, for example Tomato Yellow Leaf Curl Virus (TYLCV). The genomes of monopartite Subgroup II and III geminiviruses have an arrangement of genes similar to the AL1, AL2 and AL3 genes found on the A DNA component of bipartite Subgroup III geminiviruses.

Subgroup III viruses are also divided into "old world" and "new world" viruses, a division based on evolutionary divergence.

For successful infection of plants by bipartite geminiviruses, both the A and B genomic components are required. Examples of Subgroup II and III geminiviruses include African Cassava Mosaic Virus (ACMV) and Tomato Golden Mosaic Virus (TGMV). TGMV, like ACMV, is composed of two circular DNA molecules of the same size, both of which are required for infectivity. Sequence analysis of the two genome components reveals six open reading frames (ORFs); four of the ORFs are encoded by DNA A and two by DNA B. On both components, the ORFs diverge from a conserved 230 nucleotide intergenic region (common region) and are transcribed bidirectionally from double stranded replicative form DNA. The ORFs are named according to genome component and orientation relative to the common region (i.e., left versus right (L/R), or virion versus complementary sense (V/C)). Certain proteins are known to be involved in the replication of viral DNA (REP genes). See, e.g., Elmer et al., *Nucleic Acids Res.* 16:7043 (1988); Hatta and Francki, *Virology* 92:428 (1979).

The A genome component contains all viral information necessary for the replication and encapsidation of viral DNA, while the B component encodes functions required for movement of the virus through the infected plant. The DNA A component of these viruses is capable of autonomous replication in plant cells in the absence of DNA B when inserted as a greater than fall length copy into the genome of plant cells, or when a copy is transiently introduced into plant cells. In monopartite geminivirus genomes, the single genomic component contains all viral information necessary for replication, encapsidation, and movement of the virus.

Geminiviruses cause substantial losses among economically important crops, including tomato, bean and cucurbit. Current strategies to control geminivirus infections target the insect vectors that carry the viruses. However, the use of insecticides to control or combat a geminivirus infection can be expensive and inefficient. Additionally, insect hosts may vary in their susceptibility to available insecticides, and resistance to insecticides may develop over time. See Markham et al., *Pestic. Sci.* 42:123 (1994).

Varied approaches have been used in attempts to generate geminivirus-resistant plants, including classical breeding and transgenic approaches, with limited success. Unlike plant RNA viruses, the introduction of geminivirus sequences into transgenic plants does not confer resistance and, conversely, frequently results in the production of functional viral proteins (Hayes and Buck, *Nucleic Acids Res.* 17:10213 (1989); Hanley-Bowdoin et al., *Proc. Natl. Acad. Sci. USA* 87:1446 (1990)). Kunik et al. report transgenic tomatoes that contain a geminivirus coat protein gene (Kunik et al., *BioTechnology* 12:500 (1994)). Expression of antisense RNAs against geminivirus replication proteins in transgenic plants reduces the level of viral DNA accumulation up to 70% (Day et al., *Proc. Natl. Acad. Sci. USA* 88:6721 (1991)), to a level that is still sufficient to confer wild type viral symptoms (Hanley-Bowdoin et al., *Plant Cell* 1:1057 (1989)). Similarly, the presence of defective-interfering replicons in transformed plants can reduce the level of viral DNA accumulation by about 70% (Frischmuth and Stanley, *Virology* 200:826 (1994)). The antisense RNAs and defective-interfering replicons function best against their cognate viruses (Bejarano et al., *Plant Mol. Biol.* 24:241 (1994)), further limiting their usefulness. Antisense RNA targeted to mRNA of the Rep protein (encoded by the C1 gene) was used by Bendahmane and Gronenborn to produce transgenic *Nicotiana benthamiana* plants with altered responses to TYLCV. *Plant Mol. Biol.* 33:351 (1997)

Accordingly, it is desirable to devise new strategies to control geminivirus infection.

SUMMARY OF THE INVENTION

A first aspect of the present invention is a plant containing transformed plant cells, which contain a heterologous nucleic acid construct comprising a promoter operable in the plant cells, a nucleic acid sequence encoding a mutant AL3/C3 protein, and a termination sequence. Expression of the mutant AL3/C3 protein increases resistance of the plant to infection by at least one geminivirus, compared to a non-transformed control.

A further aspect of the present invention is a tomato plant containing transformed plant cells, which contain a heterologous nucleic acid construct comprising a promoter operable in the plant cells, a nucleic acid sequence encoding a mutant AL3/C3 protein, and a termination sequence. Expression of the mutant AL3/C3 protein increases resistance of the tomato plant to infection by at least one geminivirus, compared to a non-transformed control.

A further aspect of the present invention is a plant of the family Solanaceae containing transformed plant cells, which contain a heterologous nucleic acid construct comprising a promoter operable in the plant cells, a nucleic acid sequence encoding a mutant AL3/C3 protein, and a termination sequence. Expression of the mutant AL3/C3 protein increases resistance of the plant to infection by at least one geminivirus, compared to a non-transformed control.

A further aspect of the present invention is a method of combating geminivirus infection in an agricultural field, by planting the field with a crop of plants comprising transformed plant cells, where the transformed plant cells contain a heterologous nucleic acid construct comprising a promoter operable in the plant cells, a nucleic acid sequence encoding a mutant AL3/C3 protein, and a termination sequence. Expression of the mutant AL3/C3 protein increases resistance of the plants to infection by at least one geminivirus, compared to a non-transformed control.

A further aspect of the present invention is a method of making a transgenic plant having increased resistance to geminivirus infection, by transforming a plant cell with a DNA construct comprising a promoter, a nucleic acid sequence encoding a mutant AL3/C3 protein, and a termination sequence. A plant is then regenerated from the transformed plant cell, and expression of the mutant AL3/C3 protein increases resistance of the plant to infection by at least one geminivirus, compared to a non-transformed control.

A further aspect of the present invention is a nucleic acid construct containing a promoter operable in a plant cell, a nucleic acid sequence encoding a mutant AL3/C3 protein, and a termination sequence positioned downstream from the nucleic acid sequence.

A further aspect of the present invention is a method of producing nucleic acid constructs useful in enhancing geminivirus-resistance in plants. The method includes identifying mutants of a geminivirus AL3/C3 protein that enhance geminivirus resistance in plant cells when expressed therein, and preparing a nucleic acid construct containing a promoter operable in a plant cell, a nucleic acid sequence encoding the mutant AL3/C3 protein, and a termination sequence positioned downstream from the nucleic acid sequence.

BRIEF DESCRIPTION OF THE DRAWINGS

FIG. 3 compares the sequences of sixteen AL3/C3 geminivirus proteins and the consensus sequence.

FIG. 4 provides the sequences of thirty-one TYLCV C3 mutants.

FIG. 5 provides the sequences of six TGMV AL3 mutants.

DETAILED DESCRIPTION

The present invention now will be described more fully hereinafter with reference to the accompanying drawings, in which preferred embodiments of the invention are shown.

The present method utilizes the expression of trans-dominant mutants of the geminivirus accessory replication protein, AL3/C3 (also known as Ren), to confer increased resistance to geminiviruses in transgenic plants. While not wishing to be held to a single underlying theory, the present inventors hypothesize that the mutant proteins may interfere with the replication activity of the wild type protein produced by infecting geminiviruses, reducing the replication of infecting viruses and leading to enhanced resistance. Alternatively, the mutant proteins may interact with proteins that are required at the whole plant level, but that are not required at the plant cell level. The AL3/C3 proteins do not function in a virus-specific manner and, thus, mutant versions are useful in producing transgenic plants with enhanced resistance to multiple geminiviruses.

The present inventors determined that transgenic plants expressing trans-dominant mutant geminivirus AL3/C3 proteins have increased resistance to infection by various geminiviruses. Geminivirus AL3/C3 proteins from closely related geminiviruses (unlike AL1/C1 proteins) are functionally interchangeable, and thus the present approach results in enhanced resistance to various geminivirus infections.

The Geminiviridae family consists of three subgroups that differ with respect to insect vector, host range and genome structure. Subgroup I includes leafhopper-transmitted viruses that generally infect monocot plants and have single-component genomes. Subgroup III includes whitefly-transmitted viruses that infect dicot plants and most commonly have bipartite genomes. Subgroup II viruses are transmitted by leafhoppers and have single-component genomes like Subgroup I, but infect dicot plants like Subgroup III. Members of the three subgroups use similar replication and transcription strategies, although differences exist.

Figure 1A:
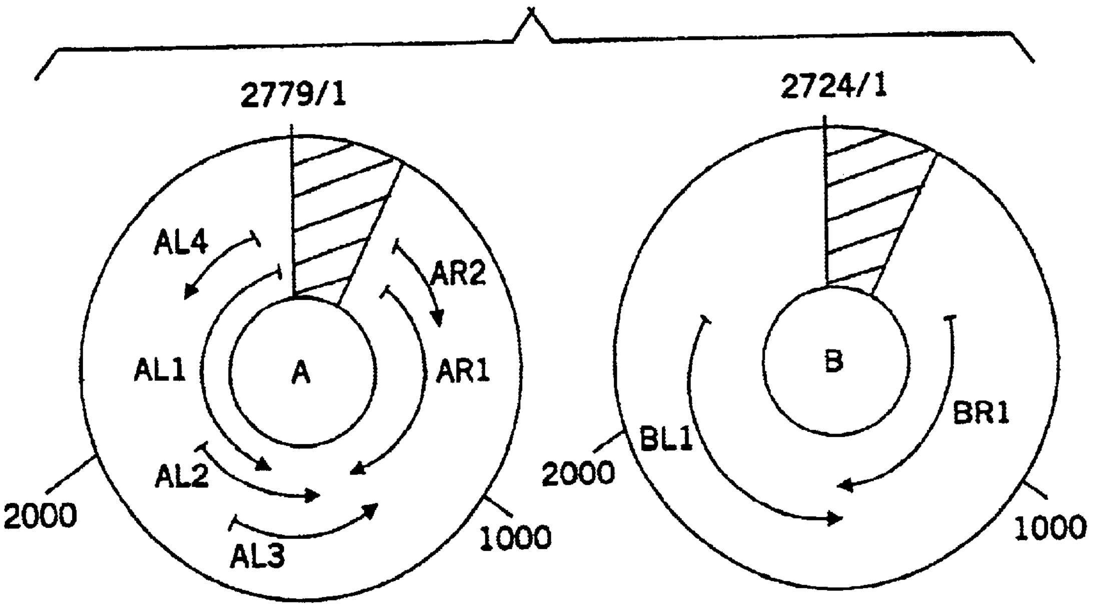
FIG. 1A provides a genome map of a representative bipartite geminivirus (African cassava mosaic virus (ACMV)). DNA A and DNA B components are shown with the location of coding regions in the virion sense (AR1, AR2) and complementary sense (AL1, AL2, AL3, AL4). The intergenic sequence is shaded.
Figure 1B:
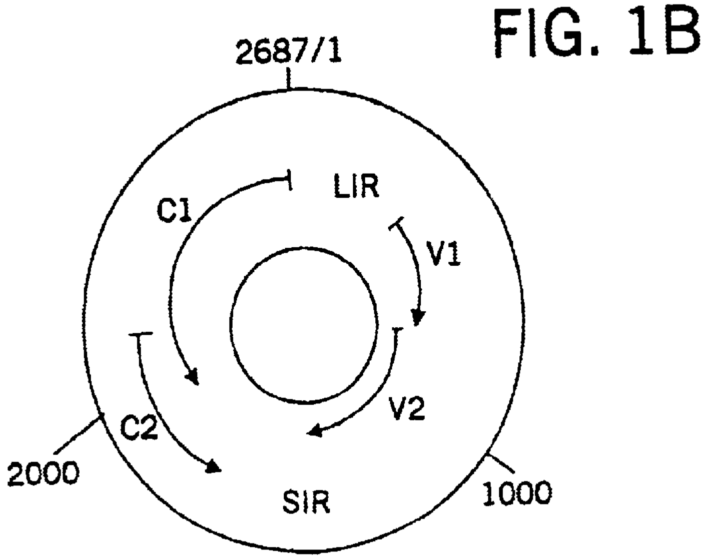
FIG. 1B provides a genome map of a representative monopartite geminivirus (maize streak virus (MSV)). The location of coding regions in the virion sense (V1, V2) and complementary sense (C1, C2) are shown. LIR refers to the large intergenic region and SIR refers to the small intergenic region.

Geminiviruses have small genomes consisting of either one or two circular ss DNA molecules ranging from about 2.5 to about $3\times10^3$ nucleotides in size. The genomic DNAs contain divergent coding sequences separated by 5' intergenic regions. The coding capacity of the genomes varies among the different subgroups. Subgroup I viruses specify four open reading frames for polypeptides greater than 10 kDa, whereas subgroup II and III viruses encode six to seven open reading frames. There are currently two nomenclatures for geminivirus genes. The first nomenclature identifies viral genes as to whether they are specified by the virion (V) or complementary (C) sense DNA strands, whereas the second designates genes with respect to the left (L) or right (R) of the 5' intergenic region (see FIGS. 1A and 1B). The C and L designations are equivalent, as are the V and R designations.

The genomes of Subgroup III geminiviruses typically consist of two DNA components, designated A and B. Both components are required for efficient infection of host plants. The A component encodes all of the information necessary for viral replication and encapsidation, whereas the B component cannot replicate in the absence of A DNA, but is required for systemic movement of the virus and symptom production in infected plants. The A component typically contains five open reading frames (ORFs), four of which (AL1/C1, AL2/C2, AL3/C3 and AL4/C4) are specified by overlapping sequences on the complementary strand. Mutations in the AL3 gene result in severely delayed and attenuated symptoms (Morris et al., *J. Gen. Virol.* 72:1205 (1991); Etessami et al., *J. Gen. Virol.* 72:1005 (1991); Sung and Coutts, *J. Gen. Virol.* 76:1773 (1995)).

AL1/C1 (Rep) and AL3/C3 proteins are involved in geminivirus replication, and AL1/C1 (Rep) and AL2/C2 proteins act in regulating viral gene expression. Mutation of the AL1 open reading frame was shown to block viral replication, whereas an AL3 mutant resulted in reduced DNA levels (Sunter et al., *Virology* 179:69 (1990); Sung and Coutts, *J. Gen. Virol.* 76:1773 (1995)). Additionally, transgenic plants that contained the AL1 gene and constitutively expressed the Rep protein in the absence of AL3 supported replication of DNA B, demonstrating that Rep is sufficient for replication in the presence of host factors. (Hanley-Bowdoin et al., *Proc. Natl. Acad. Sci. USA* 87:1446 (1990); Elmer et al. *Nucleic Acids Res.* 16:7043 (1988)).

The AL3/C3 protein enhances viral DNA accumulation of Subgroup II and III geminiviruses through an unknown mechanism. TGMV AL3 is located in nuclei of infected plant cells at levels similar to the Rep protein (Nagar et al., *Plant Cell* 7:705 (1995)). Two protein interactions have been demonstrated for TGMV and BGMV AL3: oligomerization and interaction with Rep (Settlage et al., *J. Virol.* 70:6790 (1996)). Neither of these interactions displays virus specificity, consistent with the ability of AL3/C3 proteins from different geminiviruses to functionally substitute for each other in replication assays (Sunter et al., *Virology* 203:203 (1994); Gladfelter et al., *Virology* 239:186 (1997)).

The genomes of all geminiviruses employ the same general strategy for duplication and expression: a rolling circle replication system that amplifies ssDNA and produces dsDNAs that serve as templates for replication and transcription. The double-stranded form of DNA is divergently transcribed from a 5' intergenic region that also includes the plus-strand origin of replication.

Rolling circle replication is a two-step process; synthesis of the leading and lagging-strand DNA are separate events. The single-stranded 'plus' strand is first used as a template for the synthesis of the 'minus' strand, resulting in a double-stranded replicative form (RF). The replicative form then serves as a template for plus-strand synthesis to generate free ssDNA. A site-specific nick primes plus-strand DNA synthesis (a hallmark of rolling circle replication systems). Minus-strand synthesis is primed by RNA that is most likely generated by pol $\alpha$/primase complex. (The plus strand corresponds to the virion strand found in both ssDNA and dsDNA; the minus strand is the complementary strand found only in dsDNA).

Thus, geminivirus replication requires two origins, one for plus-strand synthesis and one for minus-strand synthesis. The plus-strand origin of geminiviruses from all three Subgroups has been mapped to the 5' intergenic region, which also contains the promoters for virion and complementary-sense transcription. The cis elements that mediate viral replication and transcription are best characterized for the Subgroup III geminivirus, TGMV.

Geminiviruses fall into three subgroups based on their insect vector, host range and genome structure. Most dicot-infecting viruses have two genome components, designated A and B, and are transmitted by whiteflies. The single genome components of monopartite, dicot-infecting geminiviruses most resemble the A components of the bipartite viruses. The genome components are arranged similarly with 5' intergenic regions separating divergent transcription units. The 5' intergenic regions contain the viral replication origin (Revington et al., *Plant Cell* 1:985 (1989); Lazarowitz et al., *Plant Cell* 4:799 (1992)) and transcription signals (Eagle et al. *Plant Cell* 6:1157 (1994)).

Dicot-infecting bipartite geminiviruses encode two replication proteins, AL1 and AL3, and recruit the remainder of their replication machinery from the host plant. For monopartite dicot-infecting geminiviruses such as tomato yellow leaf curl virus (TYLCV), the equivalent proteins are designated as C1 and C3, respectively. The AL1 protein is the only viral protein essential for viral replication (Elmer et al., *Plant Mol. biol.* 10:225 (1988); Hayes and Buck, *Nucleic Acids Res.* 17:10213 (1989); Hanley-Bowdoin et al., *Proc. Natl. Acad. Sci. USA* 87:1446 (1990)). Nagar et al. report that AL1 induces the synthesis of host replication machinery in infected plant cells (Nagar et al., *Plant Cell* 7:705 (1995)). The AL3 protein is not required for replication, but enhances the level of viral DNA accumulation (Etessami et al., *J. Gen. Virol.* 72:1005 (1991); Morris et al., *J. Gen. Virol.* 72:1205 (1991)). No RNA specifying the AL3 ORF alone has been detected, suggesting that the AL3 gene product is translated from an internal ORF.

The present methods utilize expression of a partially defective (mutant) trans-dominant viral AL3/C3 protein in transgenic plants. The mutant AL3/C3 protein may interfere with the function of its wildtype counterpart, or the essential viral replication protein AL1/C1. Alternatively, the mutant AL3/C3 protein may interfere with the ability of the host plant to provide necessary replication factors.

Gronenborn and colleagues reported that *N. benthamiana* plants expressing a TYLCV C1 mutant protein are less susceptible to TYLCV infection. However, AL1 trans-dominant mutants have two disadvantages. AL1 proteins interact with DNA in a virus-specific manner (Fontes et al., *Plant Cell* 4:597 (1992); Fontes et al., *J. Biol. Chem.* 269:8459 (1994)), such that trans-dominant mutants are likely to act in a virus-specific fashion (Fontes et al., *Plant Cell* 6:405 (1994)) and to exert strong selective pressure in the field for resistance-breaking viruses. Additionally, AL1 induces the synthesis of host replication proteins (Nagar, *Plant Cell* 7:705 (1995)) by interacting with plant cell cycle regulatory factors (Ach et al., *Mol. Cell. Biol.* 17:5077 (1997), and expression can be unstable in transgenic plants.

The present inventors have determined that the AL3/C3 protein of geminiviruses is useful in producing transgenic plants with increased resistance to geminivirus infection, using a trans-dominant mutant strategy. The present inventors have determined that AL3 interacts directly with AL1 in a virus-nonspecific manner, and interacts with itself. The present inventors utilize a mutant version of AL3/C3, in which one or more of these functions is disrupted.

The present methods utilize nucleic acid constructs encoding mutated versions of naturally occurring geminivirus AL3/C3 proteins. The term "mutated" as used herein regarding proteins or polypeptides means that at least one amino acid in the wild-type or naturally occurring protein or polypeptide sequence has been replaced with a different amino acid, or deleted from the sequence. Preferably at least two or more adjacent amino acids in the wild-type sequence are replaced or deleted. Mutant AL3/C3 proteins may contain from about 2 to about 30, or more, replaced or deleted amino acids.

As used herein, the term "AL3/C3" protein refers to the geminivirus proteins that are known in the art as AL3/C3 proteins in Subgroup III geminiviruses, and as C3 proteins in Subgroup II geminiviruses. Subgroup II and III geminiviruses encode a protein that is identifiable by those skilled in the art, based on structure and/or function, as the AL3/C3 protein. As used herein, the term "AL3/C3" as it is applied to polypeptides includes fragments of AL3/C3 proteins. As used herein, the term "AL3/C3" as it is applied to nucleic acid sequences (including naturally occurring sequences and genes, and synthesized nucleic acid sequences) refers to sequences that encode a naturally occurring AL3/C3 protein or polypeptide, or a mutated AL3/C3 protein or peptide as described herein.

Mutated AL3/C3 proteins and polypeptides useful in the present methods are those which, when expressed in a plant cell, reduce the sensitivity of the cell (or a plant comprising such cells) to infection by a geminivirus. Mutated AL3/C3 proteins and polypeptides useful in the present methods are also those which, when expressed in a plant cell, increase or enhance the resistance or tolerance of the cell (or a plant comprising such cells) to infection by a geminivirus.

As used herein, "sensitivity" of a plant to infection by a geminivirus refers to the rate at which symptoms of geminivirus infection develop, and the severity of symptoms. Plants with reduced sensitivity to infection have delayed development of symptoms and/or less severe symptoms of geminivirus infection compared to that which occurs in a control plant.

As used herein, "tolerance" refers to plants that are infected with and contain a geminivirus, but do not show symptoms associated with viral infection. Tolerant crop plants are able to produce a good crop despite geminivirus infection. As used herein, plants that are "immune to infection" by a geminivirus are those in which replication of the virus is prevented. As used herein, plants that are "resistant" to infection by a geminivirus are those that show both immunity to infection and tolerance.

It will be apparent to those skilled in the art that the ability of a plant to survive and thrive when exposed to geminiviruses is a continuum, from plants that are less sensitive to infection, to those that are tolerant to infection, to those that are resistant to, geminiviruses. A plant that shows enhanced resistance or tolerance to geminivirus infection is considered herein to also show reduced sensitivity to geminivirus infection. In each case, the severity and/or rate of development of symptoms in plants with enhanced resistance (reduced sensitivity) to geminiviruses is less than that which occurs in a control plant.

Sensitivity, tolerance or resistance to geminivirus infection may be measured at the level of a plant cell or at the level of a single plant (e.g., by assessing the severity or rapidity of symptom development), or at the level of a plurality of plants (e.g., by assessing the prevalence and/or severity of infection, or the crop yield). Sensitivity in transgenic plants can be assessed by comparison to non-transformed control plants of the same species.

As used herein, the terms "protein" and "polypeptide" are used interchangeably, and refer to a polymer of amino acids (dipeptide or greater) linked through peptide bonds. Thus, the term "polypeptide" includes proteins, oligopeptides, protein fragments, protein analogs and the like. The term "polypeptide" contemplates polypeptides as defined above that are encoded by nucleic acids, are recombinantly produced, are isolated from an appropriate source, or are synthesized.

The mutated AL3/C3 proteins useful in the present methods may be based on any naturally-occurring AL3/C3 protein. A series of site-directed mutants of any AL3/C3 protein can be prepared and screened for the ability to enhance geminivirus resistance (for example, using tobacco protoplast complementation assays as described in the Examples, below). Mutant AL3/C3 proteins or polypeptides capable of reducing sensitivity to geminivirus infection in transgenic plants according to the methods herein are identified, and nucleic acid constructs capable of encoding the mutant protein are prepared according to methods known in the art, for use in producing transgenic plants with reduced sensitivity to (or increased resistance or tolerance to) geminivirus infection.

As used herein, a "native" or "naturally-ocurring" nucleic acid sequence is a sequence that is found in non-transgenic cells or tissue. Native nucleic acid sequences are thus those which have not been artificially altered, such as by site-directed mutagenesis. Once native nucleic acid sequences have been determined, molecules having these sequences can be synthesized or produced using recombinant nucleic acid procedures as are known in the art. As used herein, a native geminivirus nucleic acid sequence is that which can be isolated from a naturally-occurring geminivirus.

Mutants of AL3/C3 proteins from various geminiviruses are suitable for use in the present invention, including but not limited to: Tomato golden mosaic virus (TGMV), tomato mottle virus, tomato yellow leaf curl virus (TYLCV), tomato leaf curl virus (TLCV), potato yellow mosaic virus (PYMV), African cassava mosaic virus (ACMV), Indian cassava mosaic virus, bean golden mosaic virus (BGMV), bean dwarf mosaic virus, squash leaf curl virus, cotton leaf curl virus (CLCV), beet curly top virus (BCTV), Texas pepper virus and Pepper Huastico virus. A preferred mutant protein or polypeptide is one in which one or more amino acid residues are replaced with alanine.

The sequence of the AL3/C3 protein of the Indian cassava mosaic virus can be found at GenBank Accession No. Z24758 (Hong et al., *J. Gen. Virol.* 74:2437 (1993)); for tomato golden mosaic virus at GenBank Accession No. K02029 (Hamilton et al., *EMBO J.* 3:2197 (1984)); for tomato mottle virus at GenBank Accession No. L14460 (Abouzid et al., *J. Gen. Virol.* 73:3225 (1992)); for Taino tomato mottle virus at GenBank Accession No. AF012300 (Ramos et al., *Plant Dis.*, in press); for potato yellow mosaic virus at GenBank Accession No. D00940 (Coutts et al., *J. Gen. Virol.* 72:1515 (1991); Fontes et al., *J. Biol. Chem.* 269:8459 (1994)); for Texas pepper virus strain Tamaulipas at GenBank Accession No. U57457 (Torres-Pacheco, *Phytopathology,* 86: 1186 (1996)); for pepper Huasteco virus at GenBank Accession No. X70418 (Torres-Pacheco et al., *J. Gen. Virology* 74:2225 (1993)); for bean golden mosaic virus at GenBank Accession No. M91604 (Gilbertson et al., *Phytopathology,* 81:980 (1991)); for bean golden mosaic virus at GenBank Accession Nos. L01635 and M88686 (Gilbertson et al., *Phytopathology* 81:980 (1991); Gilbertson et al., *Plant Dis.* 75:336 (1991)); for bean dwarf mosaic virus at GenBank Accession No. M88179 (Gilbertson et al., *Phytopathology* 81:980 (1991)); and for squash leaf curl virus at GenBank Accession No. M38183 (Lazarowitz and Lazdins, *Virology* 180:58 (1991)). The present methods are useful in producing transgenic plants with enhanced resistance to one or more of the above-listed, or related, geminiviruses.

Unless otherwise stated, nucleotide sequences are presented herein by single strand only, in the 5' to 3' direction, from left to right. Nucleotides are represented herein in the manner recommended by the IUPAC-IUB Biochemical Nomenclature Commission.

The methods and constructs of the present invention are useful in transforming dicot plant species to produce plants with reduced sensitivity to geminivirus infection. Dicots suitable for use in practicing the present invention include plants from the Fabaceae, Solanaceae, Brassicaceae, Rosaceae and Compositae families. Examples of plant species suitable for transformation with the DNA constructs of the present invention include but are not limited to tobacco (*Nicotiana tabacum*), potato (*Solanum tuberosum*), soybean (*glycine max*), tomato (*Lycopersicon esculentum*), cassava (*Manihot esculenta*), beets, peanuts (*Arachis hypogaea*), cotton (*Gossypium hirsutum*), citrus trees (Citrus spp.), corn or maize (*Zea mays*), beans (e.g., green beans (*Phaseolus vulgaris*) and lima beans (*Phaseolus limensis*)), peas (Lathyrus spp.), sugarbeet, sunflower, carrot, celery, flax, cabbage and other cruciferous plants, pepper, strawberry, lettuce, alfalfa, oat, wheat, rye, rice, barley, sorghum and canola. Thus an illustrative category of plants which may be transformed with the constructs of the present invention are members of the family Solanacae, and a particular plant which may be transformed using the constructs of the present invention is cotton.

A variety of techniques are available in the art for introduction of DNA constructs into a plant cell host. These include, but are not limited to, Agrobacterium-mediated transfection, injection, electroporation, microparticle bombardment. In preferred embodiments, plants are transfected using Agrobacterium-mediated transfection, or intact plants are inoculated using microprojectiles carrying a nucleic acid construct according to the present invention.

In practice, a crop comprising a plurality of plants of the invention may be planted together in an agricultural field. By "agricultural field" is meant a common plot of soil or a greenhouse. Thus, the present invention provides a method of providing a crop of transgenic plants.

Those familiar with recombinant DNA methods available in the art will recognize that one can employ a nucleic acid sequence coding for a mutant AL3/C3 protein of the present invention, joined in the sense orientation with appropriate operably linked regulatory sequences, to construct transgenic cells and plants. Appropriate regulatory sequences for expression of nucleic acid sequences in the sense orientation include any of the known eukaryotic translation start sequences, in addition to promoter and polyadenylation/transcription termination sequences.

Nucleic acid constructs (or "transcription cassettes") of the present invention include, 5' to 3' in the direction of transcription, a promoter as discussed above and, operatively associated with the promoter, a nucleic acid sequence encoding a mutant AL3/C3 protein of the present invention. The construct may optionally contain a termination sequence including stop signal for RNA polymerase. Each of these regulatory regions should be capable of operating in the cells of the tissue to be transformed. Any suitable termination signal may be employed in carrying out the present invention, examples thereof including, but not limited to, the nos terminator, the CaMV terminator, or native termination signals derived from the same gene as the transcriptional initiation region or derived from a different gene. The term "operatively associated," as used herein, refers to nucleic acid sequences on a single nucleic acid molecule, which sequences are associated so that the function of one is affected by the other. Thus, a promoter is operatively associated with a nucleic acid sequence when it is capable of affecting the transcription of that sequence (i.e., the sequence is under the transcriptional control of the promoter). The promoter is said to be "upstream" from the sequence, which is in turn said to be "downstream" from the promoter.

The various fragments comprising the various constructs, transcription cassettes, markers, and the like may be introduced consecutively by restriction enzyme cleavage of an appropriate replication system, and insertion of the particular construct or fragment into the available site. After ligation and cloning the nucleic acid construct may be isolated for further manipulation. All of these techniques are amply exemplified in the literature (see, e.g., J. Sambrook et al., Molecular Cloning, A Laboratory Manual (2d Ed. 1989) (Cold Spring Harbor Laboratory)).

The term "nucleic acid sequence" as used herein refers to a DNA or RNA molecule, and more particularly a linear series of deoxyribonucleotides or ribonucleotides connected to one another by bonds, typically phosphodiester bonds, between the 3' and 5' carbon of the adjacent pentoses.

The term "promoter" refers to a region of a DNA sequence that incorporates the necessary signals for the efficient expression of a coding sequence. This may include sequences to which an RNA polymerase binds but is not limited thereto, and may include other sequences to which other regulatory proteins bind, together with regions involved in the control of protein translation. Promoters employed in carrying out the present invention may be promoters that are constitutively active in the subject plant cell. Numerous constitutively active promoters which are operable in plants are available. A preferred example is the 35S promoter from fig wort mosaic virus (FMV), or the Cauliflower Mosaic Virus (CaMV) 35S promoter. In the alternative, the promoter may be promoter that is spatially active or active only in a specific tissue of the plant (see e.g., U.S. Pat. No. 5,459,252 for root-specific promoters), or an inducible promoter (e.g., a promoter active in plants that is induced by specific conditions, such as wounding or infection by specific pathogens).

Methods of making transgenic (or 'recombinant') plants of the present invention, in general, involve first providing a plant cell capable of regeneration (the plant cell typically residing in a tissue capable of regeneration). The plant cell is then transformed with a DNA construct comprising a transcription cassette of the present invention (as described herein) and a transgenic plant is regenerated from the transformed plant cell. The transforming step may be carried out by any suitable technique as is known in the art, including but not limited to bombarding the plant cell with microparticles carrying the transcription cassette, infecting the cell with an *Agrobacterium tumefaciens* containing a Ti plasmid carrying the transcription cassette, or any other suitable technique.

Vectors which may be used to transform plant tissue with the nucleic acid constructs of the present invention include both Agrobacterium vectors and ballistic vectors, as well as other suitable vectors known to those in the art. *Agrobacterium tumefaciens* cells containing a nucleic acid construct of the present invention are useful in methods of making transformed plants. Plant cells are infected with an *Agro-*

*bacterium tumefaciens* to produce a transformed plant cell, and then a plant is regenerated from the transformed plant cell, according to methods known in the art. Numerous Agrobacterium vector systems useful in carrying out the present invention are known (see, e.g., U.S. Pat. No. 4,459, 355; U.S. Pat. No. 4,795,855; U.S. Pat. No. 4,940,838).

Microparticles carrying constructs of the present invention, which microparticle is suitable for the ballistic transformation of a plant cell, are also useful for making transformed plants of the present invention. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050; in Christou et al., U.S. Pat. No. 5,015,58; and in Agracetus European Patent Application Publication No. 0 270 356, titled "Pollen-mediated Plant Transformation".

Plant species may be transformed with the nucleic acid constructs of the present invention by the DNA-mediated transformation of plant cell protoplasts and subsequent regeneration of the plant from the transformed protoplasts in accordance with procedures known in the art. Fusion of tobacco protoplasts with DNA-containing liposomes or via electroporation is known in the art (Shilleto et al., *Methods in Enzymology,* 153:313–336 (1987)).

As used herein, transformation refers to the introduction of exogenous nucleic acid molecules into cells, so as to produce transgenic cells stably transformed with the exogenous nucleic acid. Transformed plant cells are induced to regenerate intact plants through application of cell and tissue culture techniques that are known in the art. The method of plant regeneration is chosen so as to be compatible with the method of transformation. The stable presence and orientation of the exogenous DNA in transgenic plants can be verified by the Mendelian inheritance of the DNA sequence, as revealed by standard methods of DNA analysis applied to progeny resulting from controlled crosses.

Any plant tissue capable of subsequent clonal propagation, whether by organogenesis or embryogenesis, may be transformed with the constructs of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Transgenic plants of the present invention may take a variety of forms. The plants may be chimeras of transformed cells and non-transformed cells; the plants may be clonal transformants (e.g., all cells transformed to contain the transcription cassette); the plants may comprise grafts of transformed and non-transformed tissues. The transformed plants may be propagated by a variety of means known in the art, such as by clonal propagation or by classical breeding techniques.

The examples which follow are set forth to illustrate the present invention, and are not to be construed as limiting thereof.

EXAMPLE 1

Construction of TYLCV C3 and TGMV AL3 Mutants

TYLCV C3 and TGMV AL3 site-directed mutants were generated containing substitutions of conserved amino acid residues. The mutants were analyzed in tobacco protoplast complementation assays.

Figure 2:
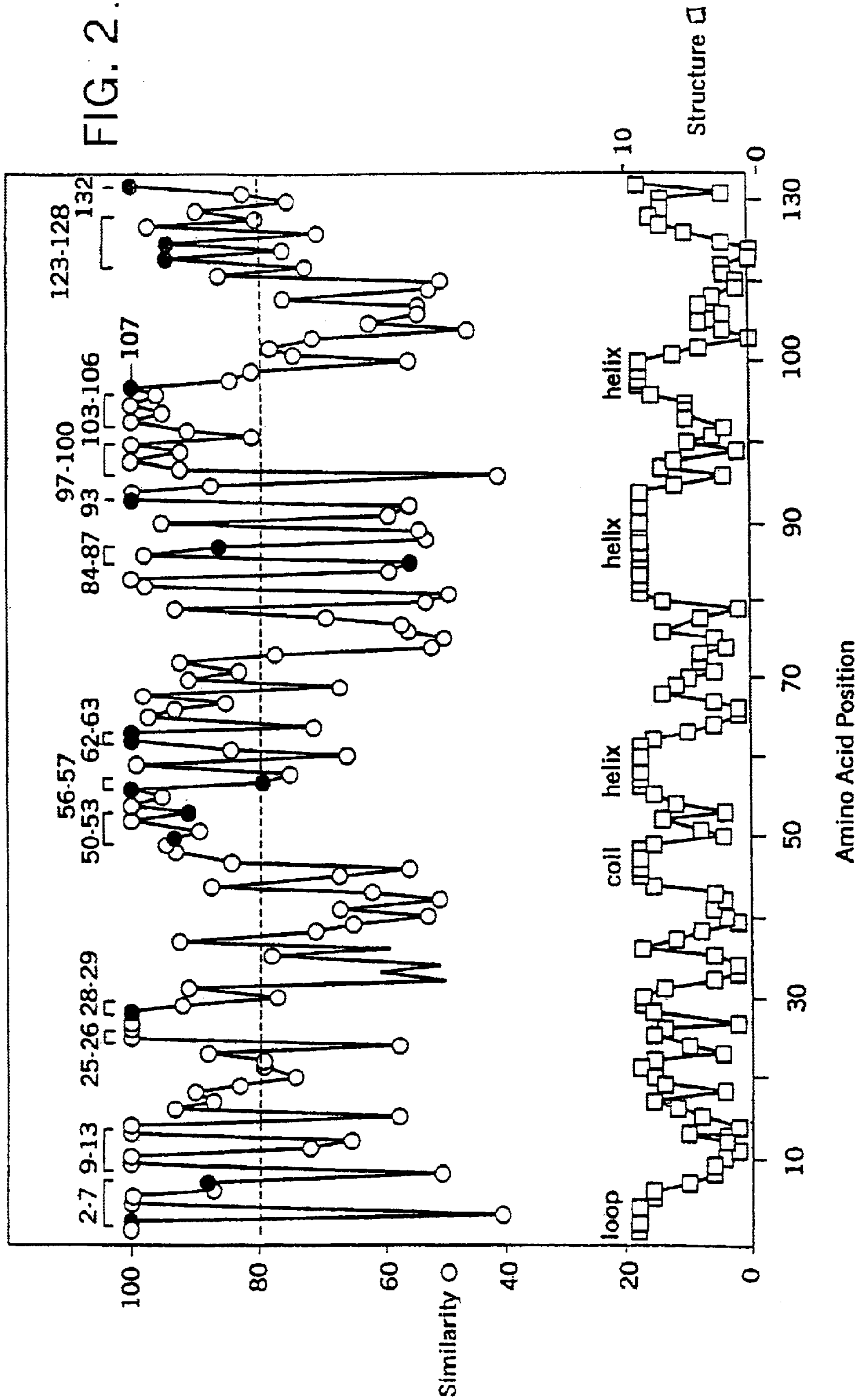
FIG. 2 provides a comparison of the sequences of 13 AL3/C3 proteins using the EMBL Predict program, which assigns a similarity score to each amino acid position and predicts protein secondary structure based on all of the protein sequences. The 13 AL3/C3 proteins showed an overall similarity score of about 80% and included long stretches of predicted α-helical structure.

The AL3/C3 proteins are highly conserved among different geminiviruses. The sequences of sixteen AL3/C3 proteins (and the consensus sequence) are compared in FIG. 3 using the EMBL Predict program (Rost and Sander *J. Mol. biol.* 232:585 (1993)). This program assigns a similarity score to each amino acid position and predicts protein secondary structure based on all of the protein sequences. FIG. 2 plots, for thirteen AL3/C3 proteins, the similarity scores for each amino acid position (circle) with 100 indicating identity at that position among all thirteen sequences. These thirteen AL3/C3 proteins showed an overall similarity score of about 80% (dashed line). Charged amino acids are marked by filled circles and conserved tyrosines or histidines are indicated by shaded circles. The structural prediction scores are also plotted in FIG. 2 (squares), with 9 indicating a 90% probability that a given amino acid will be part of the predicted structure. The structural motifs predicted at high probability are labeled (loop,coil, helix). The thirteen AL3/C3 proteins included long stretches of predicted α-helical structure. This information was used to identify, cluster and prioritize mutations to be introduced into the TYLCV C3 coding sequence.

Mutations were introduced into the TYLCV C3 and TGMV AL3 coding sequences by site-directed mutagenesis (Kunkel, *Proc. Natl. Acad. Sci USA* 82:482 (1985)) and verified by DNA sequencing. The mutated coding sequences were subcloned into a plant expression cassette (pMON10018 or equivalent) containing the FMV (fig mosaic virus) promoter and NOS terminator which are flanked by NotI restriction sites. The mutant coding sequences were also cloned downstream of the polyhedrin promoter of pMON27025, a transfer vector that allows the generation of recombinant baculovirus DNA in *Escherichia coli* (Luckow et al., *J. Virol.* 67:4566 (1993)).

Thirty-one TYLCV C3 mutants were produced (SEQ ID NOs:18–48), as shown in FIG. 4. Mutants were numbered in order of preparation; in some cases, mutant sequences represent a combination or extension of earlier-created mutant sequences (e.g., mutant#69 (SEQ ID NO:45) incorporates the sequence changes of mutants #21 and #45 (SEQ ID NOs: 21 and 33)).

Six TGMV AL3 mutants were produced (SEQ ID NOS: 49–54), as shown in FIG. 5.

EXAMPLE 2

TYLCV and TGMV Constructs

A 1.5 copy TYLCV replicon plasmid with a deletion in the C3 open reading frame (pTYLC7) and an FMV promoter/wildtype full-length C3 ORF/nos terminator plant expression cassette were constructed and used to establish a C3 complementation assay (Fontes et al., *J. Biol. Chem.* 269:8459 (1994); Gladfelter et al., *Virology* 239:186 (1997)). The TYLCV replicon with the deleted C3 ORF replicated inefficiently when electroporated into tobacco protoplasts, and viral DNA accumulation was assayed by DNA blot analysis. When the FMV promoter/wildtype full-length C3 ORF/nos cassette was co-introduced into protoplasts, it complemented the defect in the TYLCV C3 mutant replicon, resulting in high levels of viral DNA replication.

A mutant fig wort mosaic virus (FMV)-C3-E9 expression cassette containing a truncated TYLCV C3 open reading frame (pTYLC77) was also constructed.

Thirty-one mutant FMV-C3-E9 open reading frames and corresponding expression cassettes were constructed. All of the mutants were sequenced before subcloning; sequences are provided in FIG. 4.

Six site-directed mutants of the TGMV AL3 open reading frame were constructed (SEQ ID NOs:49–54); these corresponded to TYLCV C3 mutants mC3#17, mC3#67, mC3#69, mC3#71, mC3#73 and mC3#75. See FIG. 5. E35S-AL3-E9 expression cassettes corresponding to these six TGMV AL3 mutants were also constructed.

Recombinant baculovirus transfer vectors for mutant TGMV AL3 proteins of SEQ ID NOs:49–54 were constructed using techniques known in the art.

EXAMPLE 3

TYLCV-C3 Mutant Proteins

Complementation of C3 or AL3 Defective Replicons

A wild type TYLCV-DR clone (pTYLC2) was tested for replication in tobacco protoplasts, and demonstrated that the clone is functional. A C1 mutant version of TYLCV failed to replicate in tobacco protoplasts, showing that TYLCV replication is dependent on C1 and is not an artifact.

Expression cassettes containing the C3 mutants mC3#21, mC3#23, and double mutant mC3#31, were compared in tobacco protoplast-based replication assays using the TYLCV C3 mutant replicon (pTYLCV7), to test the C3 mutants' ability to provide functional C3 in trans. No enhancement of TYLCV replication was detected in the presence of mC3#17 or mC3#31, whereas mC3#21 and mC3#23 both showed low levels of complementation (about 50% of wild type C3 activity based on phosphorimage analysis). (Data not shown.) These results demonstrate that combination of the mutations in mC3#17 and mC3#31 result in a nonfunctional protein. Because of the presence of a double mutation, mC3#31 may prove to be less subject to reversion and, thus, more durable in the field.

Plasmids containing the C3 mutants mC3#17, mC3#21, mC3#23, and double mutant mC3#31, were also compared in tobacco protoplast-based replication assays using the TGMV AL3 mutant replicon, to assess their ability to complement a TGMV AL3 mutant replicon. The plant expression cassettes containing the mutant TYLCV C3 coding sequences were co-transfected into tobacco protoplasts with a modified TGMV A replicon that included an 88-bp deletion in the AL3 open reading frame, and assayed for TGMVA replication by DNA gel blotting.

The same results were obtained with this heterologous TGMV geminivirus system as with the homologous TYLCV system described above, thereby supporting the concept of broad-based resistance strategies. (Data not shown.)

An additional twenty-two C3 mutant expression cassettes (mC3#33 to mC3#75) were analyzed in replication assays using the TYLCV C3(−) replicon. C3 Mutants #67, 69, 71 and 73 had no detectable levels of C3 activity. Mutants #39, 45, 47, 53, 57 supported significantly less TYLCV replication than the wild type C3 expression cassette. TABLE 1

The mutants pTYLC51 to pTYLC75 were also assessed in replication assays using the TGMV AL3 mutant replicon (heterologous geminivirus replicon). The same results were obtained with this heterologous geminivirus system as with the homologous TYLCV replication assay described above. These results indicate that C3 function is highly conserved.

TABLE 1

| C3 Activity | TYLCV C3 Mutant |
|---|---|
| None | mC3 #17 |
| | mC3 #31 |
| | mC3 #67 |
| | mC3 #69 |
| | mC3 #71 |
| | mC3 #73 |
| Reduced | mC3 #21 |
| | mC3 #23 |
| | mC3 #47 |
| | mC3 #39 |
| | mC3 #53 |
| | mC3 #45 |
| | mC3 #57 |
| | mC3 #75 |
| Wild Type | mC3 #15 |
| | mC3 #19 |
| | mC3 #25 |
| | mC3 #27 |
| | mC3 #29 |
| | mC3 #33 |
| | mC3 #35 |
| | mC3 #37 |
| | mC3 #41 |
| | mC3 #43 |
| | mC3 #49 |
| | mC3 #51 |
| | mC3 #55 |
| | mC3 #59 |
| | mC3 #61 |
| | mC3 #63 |
| | mC3 #65 |

EXAMPLE 4

TGMV AL3 Mutant Proteins

Complementation of Defective Replicons

A plant expression cassette corresponding to TGMV AL3 that complements both TGMV and BGMV AL3-defective replicons was developed. The TGMV AL3 mutant expression cassettes were assayed in replication assays using a TGMV AL3 mutant replicon (pNSB5)

Tobacco protoplasts containing the TGMV AL3-defective replicons were transfected with either wild-type TGMV AL3, mAL3#17, mAL3#67, mAL3#69, mAL3#71, mAL3#73 or mAL3#75 expression cassettes and the pNSB5 replicon, and were analyzed for TGMV A replication by DNA gel blotting.

The AL3 mutants displayed phenotypes similar to their TYLCV C3 counterparts. Four of the TGMVmAL3 mutant proteins (mAL3#67, mAL3#69, mAL3#71 and mAL3#73) could not complement an AL3 deletion in TGMV A in these replication assays (data not shown). Mutant mAL3#17 displayed little complementation, whereas mAL3#75 was wild type.

EXAMPLE 5

AL3 Interference Assays

Titration of a wild type AL1 expression cassette established that 4 μg of the wild type cassette supported half maximal replication of TGMV B (10 μg) in the presence of wild type AL3 expression cassette (20 μg). Between 6–8 μg, AL1 expression cassette levels were saturating and thus might mask interference. (Data not shown.)

Titration of a wild type AL3 expression cassette established that 2.5 μg of the wild type cassette supported half maximal replication of a TGMV AL3 mutant replicon (10 μg) in the presence of wild type TGMV AL1 expression cassette (4 μg). At 5 μg, AL3 expression cassette levels were saturating and thus would mask interference. (Data not shown.)

These transient replication assays identified conditions for testing mutant TGMV AL3 proteins for interference with wild type AL3 function. Based on these results, interference assays included 10 μg TGMV B replicon and 4 μg each of AL1 and AL3 expression cassettes. These conditions ensured that neither viral replication protein was in excess.

EXAMPLE 6

Interference Assays—TGMV

Interference assays were performed using the conditions noted in Example 5. Tobacco protoplasts were transfected with 10 μg of TGMV B replicon, 4 μg of a TGMV AL1 expression cassette, and an expression cassette for either wildtype TGMV AL3, mAL3#17, mAL3#67, mAL3#69, mAL3#71 or mAL3#73. Protoplasts were analyzed for TGMV replication by DNA gel blotting. The wild type AL3 cassette was at 2.5 μg and the mutant AL3 cassettes were at 50 μg.

None of the TGMV AL3 mutants interfered with wild type AL3 in transient assays containing a TGMV B replicon and an AL1 expression cassette (data not shown). The assays were performed with a 20-fold excess of mutant versus wild-type AL3 expression cassette.

The present experiment, in which AL1 was also provided from an expression cassette, ruled out the possibility that the lack of interference by AL3 was due to higher level expression of the AL1 protein from an amplified template.

EXAMPLE 7

Interference Assays—TYLCV

Titration of the wild type C3 expression cassette established that 0.2 μg of the wild type C3 expression cassette supported half maximal replication of 5 μg TYLCV C3(−) mutant replicon. At 0.5 μg, C3 expression cassette levels are saturating and would probably preclude interference.

These quantities were used in interference assays containing 100- or 200-fold excess of a mutant C3 expression cassette. The assays were repeated in duplicate. No replication interference was seen for any of the mutant C3 expression cassettes. (Data not shown.)

The ability of mutant TYLCV C3 expression cassettes to interfere with the activity of a wild type C3 expression cassette in protoplast assays was tested. Interference was assayed using 10 μg TYLCV C3(−) replicon, 0.2 μg wild type TYLCV C3 expression cassette and the following amounts of mutant expression cassette: 20 μg of TYLCV C3 mutant mC3#17, mC3#67, mC3#69, mC3#71 or mC3#73; 40 μg TYLCV C3 mutant mC3#17, mC3#67, mC3#69, mC3#71, mC3#73 or mC3#77. (The C3mutants were chosen based on the earlier experiments showing that they do not complement a C3 mutant replicon in protoplasts). No interference was detected at 100- or 200-fold excess of any of the mutant expression cassettes. Based on these experiments, it was concluded that a TYLCV-based protoplast interference assay is not feasible.

EXAMPLE 8

Biochemical Analysis of Recombinant Proteins

It was established that mAL3#17, mAL3#67, mAL3#69, mAL3#71, mAL3#73 and mAL3#75 proteins are stably produced in insect cells (SF9 cells) using techniques known in the art (Luckow et al., *J. Virology* 67:4566 (1993); Settlage et al., *J. Virology* 70:6790 (1996)) (data not shown). It was also shown that mAL3#17 and mAL3#75 interact with TGMV AL1 in insect cells (data not shown). Thus, failure of mAL3#17 and mAL3#75 to support enhanced TGMV replication in complementation assays is not due to poor protein production or the inability to bind AL1. These results support the use of mAL3#17 in geminivirus resistance strategies.

Localization of TGMV AL3 wild type and mutant proteins was studied in insect cells. Cytoplasmic and nuclear extracts were prepared from SF9 cells and analyzed for AL3 protein by immunoblotting. These experiments showed that mutant AL3 proteins can get into the nuclei of insect cells (data not shown).

The present experiments established that mAL3 proteins are stably produced in a eucaryotic system (insect cells), which indicates that their negative phenotypes in replication assays is not due to lack of stable protein. These experiments also showed that mAL3 mutant proteins (mAL#17, mAL3#67, mAL3#69, mAL3#71 and mAL3#73) interact with TGMV AL1 in insect cells. These experiments indicate that there are differences in the interaction affinities of the various mutants.

EXAMPLE 9

Enhancing Trans-dominant Negative Effect—Jun. 30, 1998

The interaction between wildtype TGMV AL3 and TGMV AL1 have been detected and quantitated in a yeast dihybrid assay (Fields and Song, *Nature* 340:245 (1989)) using GAL4 DNA binding domain and GAL4 activation domain fusions (data not shown). This assay is also useful in identifying AL3 and C3 mutants with increased affinity for AL1 or C1, respectively. The identified mutant proteins are then assessed for enhanced trans-dominant negative effects in plants transformed to express the mutant proteins. Mutant proteins with increased affinity may be combined with a replication defective C3 or AL3 mutant and assessed for enhanced trans-dominant negative effects in recombinant plants.

EXAMPLE 10

Tomato Mottle Virus

The above series of experiments are repeated using the genome of the tomato mottle virus (ToMoV), an agronomically important bipartite geminivirus. Mutant TOMOV AL3 proteins are constructed and assayed as described above, to identify mutants useful in producing transgenic plants with increased resistance to geminivirus infections.

The AL3 protein sequence for tomato mottle virus is provided at GenBank Accession No. L14460 (Abouzid et al., *J. Gen. Virol.* 73:3225 (1992)) and is: MDSRTGELIT AHQAENGVYI WELENPLYFK IHRVEDPLYT RTRVYHVAIR FNHNLRKALH LHKAYLNFQV WTTSMTASGS IYLARFRYLV NMYLDQLGVI SINNVVRAVR FATNRVYVNH VLENHSIKFK FY (SEQ ID NO:17).

EXAMPLE 11

Field Tests

Agrobacterium transformation (using methods known in the art) is used to produce transformed tomato plants expressing mutant C3 or AL3 proteins as described above. Mutant C3 and AL3 constructs may initially be chosen based on the inability to complement defective geminivirus replicons (see Examples 3 and 4, above). Transformed plants are planted in a field in an area experiencing a natural epidemic of geminivirus infection, or are artificially exposed to geminivirus infection in a controlled environment. For example, transformed and control plants may be planted in fields in areas of Florida experiencing an epidemic of TYLCV-DR geminivirus infection.

Of the transformed plants exposed to geminivirus infection, some will not show any signs of infection whereas others will show delayed symptoms of infection, or a reduced severity of symptoms (compared to non-transformed control plants). Compared to non-transformed (wild-type) control plants, transformed plants will have fewer individuals showing signs of geminivirus infection; of those transformed plants showing signs of geminivirus infection, the symptoms will be delayed (on average) compared to control plants, and/or will be less severe (on average) compared to control plants.

The foregoing examples are illustrative of the present invention, and are not to be construed as limiting thereof. The invention is described by the following claims, with equivalents of the claims to be included therein.

What is claimed is:

1. An isolated nucleic acid construct comprising an expression cassette, which construct comprise , in the 5' to 3' direction, (a) a promoter operable in plant cell, (b) a nucleic acid sequence encoding a mutant AL3/C3 protein, said nucleic acid sequence located downstream from said promoter and operatively associated therewith, and (c) a termination sequence positioned downstream from said nucleic acid sequence and operatively associated therewith;

wherein said nucleic acid sequence encoding a mutant AL3/C3 protein comprises a nucleotide sequence encoding a protein having a sequence selected from the group consisting of:

SEQ ID NO: 19 and

SEQ ID NO: 26.

2. A plant comprising transformed plant cells, said transformed plant cells containing the nucleic acid construct according to claim 1, wherein said nucleic acid construct is heterologous to said plant cells, and wherein expression of said mutant AL3/C3 protein reduces sensitivity of said plant to infection by at least one geminivirus, compared to a non-transformed control.

3. The plant according to claim 2, wherein said plant has reduced sensitivity to a geminivirus selected from the group consisting of tomato golden mosaic virus, tomato mottle virus, tomato yellow leaf curl virus, tomato leaf curl virus, African cassava mosaic virus, Indian cassava mosaic virus, potato yellow mosaic virus, bean golden mosaic virus, bean dwarf mosaic virus, squash leaf curl virus, Texas pepper virus, cotton leaf curl virus and beet curly top virus.

4. The plant according to claim 2, wherein said promoter is constitutively active in said plant.

5. The plant according to claim 2, wherein said plant is selected from the group consisting of tomato, cassava, potato, bean, squash and beet.

6. A tomato plant comprising transformed tomato plant cells, said transformed tomato plant cells containing the nucleic acid construct according to claim 1, wherein said nucleic acid construct is heterologous to said tomato plant cells, and wherein expression of said mutant AL3/C3 protein reduces sensitivity of said tomato plant to infection by at least one geminivirus, compared to a non-transformed control.

7. The tomato plant according to claim 6, wherein said tomato plant has reduced sensitivity to geminivirus selected from the group consisting of tomato golden mosaic virus, tom to mottle virus, tomato yellow leaf curl virus and tomato leaf curl virus.

8. A plant of the family Solanaceae, wherein cells of said plant are transformed to contain the nucleic acid construct according to claim 1, wherein said nucleic acid construct is heterologous to said cells, and wherein expression of said mutant AL3/C3 protein reduces sensitivity of said plant to infection by at least one geminivirus, compared to a non-transformed control.

9. A method of combating geminivirus infection in an agricultural field, comprising planting the field with a crop of plants comprising transformed plant cells, said transformed plant cells containing the nucleic acid construct according to claim 1, wherein said nucleic acid construct is heterologous to said cells, and wherein expression of said mutant AL3/C3 protein reduces sensitivity of said plants to infection by at least one geminivirus, compared to a non-transformed control.

10. A method of making a transgenic plant having reduced sensitivity to geminivirus infection, said method comprising:

providing a plant cell capable of regeneration;

transforming said plant cell with the nucleic acid construct according to claim 1, wherein said nucleic ac d construct is a DNA construct; and then regenerating a transgenic geminivirus-resistant plant from said transformed plant cell, wherein expression of said mutant AL3/C3 protein reduces sensitivity of said plant to infection by at least one geminivirus, compared to a non-transformed control.

11. The method according to claim 10, wherein said plant cell resides in a plant tissue capable of regeneration.

12. A method according to claim 10, wherein said transforming step is carried out by bombarding said plant cell with microparticles carrying said expression cassette.

13. A method according to claim 10, wherein said transforming step is carried out by infecting said cells with an *Agrobacterium tumefaciens* containing a Ti plasmid carrying said expression cassette.

14. Seed or progeny of the plant according to claim 2, wherein said seed or progeny has inherited said nucleic acid sequence encoding a mutant AL3/C3 protein.

15. Seed or progeny of the plant according to claim 6, wherein said seed or progeny has inherited said nucleic acid sequence encoding a mutant AL3/C3 protein.

16. Seed or progeny of the plant according to claim 8, wherein said seed or progeny has inherited said nucleic acid sequence encoding a mutant AL3/C3 protein.

17. A DNA plant transformation vector comprising the nucleic acid construct according to claim 1.

18. The nucleic acid construct according to claim 1, wherein said nucleic acid sequence encoding a mutant AL3/C3 protein comprises a nucleotide encoding a protein having a sequence of SEQ ID NO: 19.

19. The nucleic acid construct according to claim 1, wherein said nucleic acid sequence encoding a mutant AL3/C3 protein comprises a nucleotide encoding a protein having a sequence of SEQ ID NO: 26.

* * * * *

UNITED STATES PATENT AND TRADEMARK OFFICE

CERTIFICATE OF CORRECTION

PATENT NO. : 6,747,188 B2
APPLICATION NO. : 09/164615
DATED : June 8, 2004
INVENTOR(S) : Hanley-Bowdoin et al.

It is certified that error appears in the above-identified patent and that said Letters Patent is hereby corrected as shown below:

Column 4, lines 8-12 should read:

-- Figures 3A-C provide a comparison of the sequences of sixteen AI3/C3 geminivirus proteins and the consensus sequence.

Figures 4A-D provide the sequences of thirty-one TYLCV C3 mutants.

Figures 5A-C provide the sequences of six TGMV AL3 mutants. --

Column 12, line 12 should read -- proteins (and the consensus sequence) are compared in FIGS. 3A-3C. --

Column 12, line 45 should read -- NOs: 18-48), as shown in FIGS. 4A-4D. Mutants were numbered in --

Column 12, line 52 should read -- 49-54), as shown in FIGS. 5A-5C. --

Column 13, line 10 should read -- are provided in FIGS. 4A-4D. --

Column 13, line 14 should read -- mC3#69, mC3#71, mC3#73 and mC3#75. See FIGS. 5A-5C. --

Column 69, line 34 should read -- tomato mottle virus, tomato yellow leaf curl virus and tomato --

Column 70, line 12 should read -- construct according to claim 1, wherein said nucleic acid --

Column 20, line 21 should read -- 12. The method according to claim 10, wherein said trans- --

Column 20, line 24 should read -- 13. The method according to claim 10, wherein said trans- --

Signed and Sealed this
Fourth Day of September, 2012

David J. Kappos
*Director of the United States Patent and Trademark Office*

```
                          SEQUENCE LISTING


<160> NUMBER OF SEQ ID NOS: 54

<210> SEQ ID NO 1
<211> LENGTH: 137
<212> TYPE: PRT
<213> ORGANISM: Artificial Sequence
<220> FEATURE:
<223> OTHER INFORMATION: Description of Artificial Sequence: consensus
      geminivirus C3 sequence
<220> FEATURE:
<221> NAME/KEY: VARIANT
<222> LOCATION: (26)
<220> FEATURE:
<221> NAME/KEY: VARIANT
<222> LOCATION: (50)
<220> FEATURE:
<221> NAME/KEY: VARIANT
<222> LOCATION: (77)
<220> FEATURE:
<221> NAME/KEY: VARIANT
<222> LOCATION: (83)
<220> FEATURE:
<221> NAME/KEY: VARIANT
<222> LOCATION: (87)
<220> FEATURE:
<221> NAME/KEY: VARIANT
<222> LOCATION: (90)
<220> FEATURE:
<221> NAME/KEY: VARIANT
<222> LOCATION: (113)
<223> OTHER INFORMATION: Consensus geminivirus C3 sequence.  Amino acid
      residues that vary among geminiviruses are indicated as Xaa.

<400> SEQUENCE: 1

Met Val Met Asp Ser Arg Thr Gly Glu Leu Ile Thr Ala His Gln Ala
  1               5                  10                  15

Glu Asn Gly Val Tyr Ile Trp Glu Ile Xaa Asn Pro Leu Tyr Phe Lys
             20                  25                  30

Ile Thr Arg Val Glu Asp Pro Pro Tyr Thr Arg Thr Arg Ile Tyr His
         35                  40                  45

Thr Xaa Gln Ile Arg Phe Asn His Asn Leu Arg Lys Ala Leu Gly Leu
     50                  55                  60

His Lys Ala Phe Leu Asn Phe Gln Val Trp Thr Thr Xaa Gln Thr Ala
 65                  70                  75                  80

Ser Gly Xaa Thr Tyr Leu Xaa Arg Phe Xaa Tyr Leu Val Leu Lys Tyr
                 85                  90                  95

Leu Asp Asn Leu Gly Val Ile Ser Ile Asn Asn Val Ile Arg Ala Val
             100                 105                 110

Xaa Phe Ala Thr Phe Asp Val Ser Tyr Val Thr Ile Asp Val Leu Glu
        115                 120                 125
```

-continued

```
Asn His Glu Ile Lys Phe Lys Phe Tyr
    130                 135


<210> SEQ ID NO 2
<211> LENGTH: 131
<212> TYPE: PRT
<213> ORGANISM: TYLCV - Dominican Republic isolate

<400> SEQUENCE: 2

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 3
<211> LENGTH: 134
<212> TYPE: PRT
<213> ORGANISM: TYLCV - Israeli isolate

<400> SEQUENCE: 3

Met Asp Leu Arg Thr Gly Glu Tyr Ile Thr Ala His Gln Ala Thr Ser
  1               5                  10                  15

Gly Val Tyr Thr Phe Gly Ile Thr Asn Pro Leu Tyr Phe Thr Ile Thr
             20                  25                  30

Arg His Asn Gln Asn Pro Phe Asn Asn Lys Tyr Asn Thr Leu Thr Phe
         35                  40                  45

Gln Ile Arg Phe Asn His Asn Leu Arg Lys Glu Leu Gly Ile His Lys
     50                  55                  60

Cys Phe Leu Asn Phe His Ile Trp Thr Thr Leu Gln Ser Pro Thr Gly
 65                  70                  75                  80

His Phe Leu Arg Val Phe Lys Tyr Gln Val Cys Lys Tyr Leu Asn Asn
                 85                  90                  95

Leu Gly Val Ile Ser Leu Asn Asn Val Val Arg Ala Val Asp Tyr Val
            100                 105                 110

Leu Phe His Val Phe Glu Arg Thr Ile Asp Val Thr Glu Asn His Glu
        115                 120                 125

Ile Lys Phe Asn Phe Tyr
    130


<210> SEQ ID NO 4
<211> LENGTH: 134
<212> TYPE: PRT
<213> ORGANISM: Indian cassava mosaic virus
```

-continued

<400> SEQUENCE: 4

```
Met Asp Ser Arg Thr Gly Glu Leu Ile Thr Ala Ala Gln Ala Met Asn
  1               5                  10                  15

Gly Val Phe Ile Trp Glu Val Pro Asn Pro Leu Tyr Phe Lys Ile Ile
             20                  25                  30

Gln His Asp Asn Arg Pro Phe Val Met Asn Gln Asp Ile Ile Thr Val
         35                  40                  45

Gln Ile Arg Phe Asn His Asn Leu Arg Lys Ala Leu Gly Leu His Gln
     50                  55                  60

Cys Trp Met Asp Phe Lys Val Trp Thr Thr Leu Gln Pro Gln Thr Trp
 65                  70                  75                  80

Arg Phe Leu Arg Val Phe Lys Thr Gln Val Leu Lys Tyr Leu Asp Ser
                 85                  90                  95

Leu Gly Val Ile Ser Ile Asn Thr Ile Val Lys Ala Val Glu His Val
            100                 105                 110

Leu Tyr Asn Val Ile His Gly Thr Asp Arg Val Glu Gln Ser Asn Leu
        115                 120                 125

Ile Lys Leu Asn Ile Tyr
    130
```

<210> SEQ ID NO 5
<211> LENGTH: 134
<212> TYPE: PRT
<213> ORGANISM: TYLCU

<400> SEQUENCE: 5

```
Met Asp Leu Arg Thr Gly Glu Tyr Ile Thr Ala His Gln Ala Thr Ser
  1               5                  10                  15

Gly Val Tyr Thr Phe Glu Ile Thr Asn Pro Leu Tyr Phe Thr Ile Thr
             20                  25                  30

Arg His Asn Gln Gln Pro Phe Asn Ser Lys Tyr Asn Phe Leu Thr Phe
         35                  40                  45

Gln Ile Arg Phe Asn His Asn Leu Arg Lys Ala Leu Gly Ile His Lys
     50                  55                  60

Cys Phe Leu Asn Phe Arg Ile Trp Thr Thr Leu Gln Ser Pro Thr Gly
 65                  70                  75                  80

His Phe Leu Arg Val Phe Arg Tyr Gln Val Tyr Lys Tyr Leu Asn Asn
                 85                  90                  95

Ile Gly Val Ile Ser Leu Asn Asn Val Ile Arg Ala Val Asp Tyr Val
            100                 105                 110

Leu Phe Asp Val Phe Glu Asn Thr Ile Asp Val Ile Glu Gln His Glu
        115                 120                 125

Ile Lys Tyr Asn Leu Tyr
    130
```

<210> SEQ ID NO 6
<211> LENGTH: 134
<212> TYPE: PRT
<213> ORGANISM: TYLCV Australian isolate

<400> SEQUENCE: 6

```
Met Asp Ser Arg Thr Gly Glu Pro Ile Thr Ala Arg Gln Ala Met Asn
  1               5                  10                  15

Gly Glu Tyr Ile Trp Arg Val Pro Asn Pro Leu Tyr Phe Lys Ile Ile
             20                  25                  30
```

-continued

```
Lys His His Lys Arg Pro Phe Asn Tyr Asn His Asp Ile Ile Gln Val
        35                  40                  45

Arg Ile Gln Phe Asn His Asn Leu Arg Arg Ala Leu Ala Ile His Lys
    50                  55                  60

Cys Phe Leu Asp Phe Thr Val Phe Thr Arg Leu Gln Pro Ala Thr Trp
65                  70                  75                  80

Arg Phe Leu Arg Val Phe Lys Thr Gln Val Met Lys Tyr Leu Asp Ser
                85                  90                  95

Leu Gly Val Ile Ser Ile Asn Asn Val Ile Arg Ser Val Asp His Val
            100                 105                 110

Leu Tyr Asn Val Leu Asp Ser Thr Phe Asp Val Ile Glu Asp His Asp
        115                 120                 125

Ile Lys Phe Asn Phe Tyr
    130


<210> SEQ ID NO 7
<211> LENGTH: 134
<212> TYPE: PRT
<213> ORGANISM: TYLCM

<400> SEQUENCE: 7

Met Asp Leu Arg Thr Gly Glu Tyr Ile Thr Ala His Gln Ala Thr Ser
1               5                   10                  15

Gly Val Tyr Thr Phe Gly Ile Thr Asn Pro Leu Tyr Phe Thr Ile Thr
            20                  25                  30

Arg His Asn Gln Asn Pro Phe Asn Asn Lys Tyr Asn Thr Leu Thr Phe
        35                  40                  45

Gln Ile Arg Phe Asn His Asn Leu Arg Lys Glu Leu Gly Ile His Lys
    50                  55                  60

Cys Phe Leu Asn Phe His Ile Trp Thr Thr Leu Gln Ser Pro Thr Gly
65                  70                  75                  80

His Phe Leu Arg Val Phe Lys Tyr Gln Val Cys Lys Tyr Leu Asn Asn
                85                  90                  95

Leu Gly Val Ile Ser Leu Asn Asn Val Val Arg Ala Val Asp Tyr Val
            100                 105                 110

Leu Phe His Val Phe Glu Arg Thr Ile Asp Val Thr Glu Asn His Glu
        115                 120                 125

Ile Lys Phe Asn Phe Tyr
    130


<210> SEQ ID NO 8
<211> LENGTH: 134
<212> TYPE: PRT
<213> ORGANISM: African cassava mosaic virus

<400> SEQUENCE: 8

Met Asp Leu Arg Thr Gly Glu Leu Ile Thr Ala Pro Gln Ala Met Asn
1               5                   10                  15

Gly Val Tyr Thr Trp Glu Ile Asn Asn Pro Leu Tyr Phe Thr Ile Thr
            20                  25                  30

Arg His Gln Gln Arg Pro Phe Leu Leu Asn Gln Asp Ile Ile Thr Val
        35                  40                  45

Gln Val Arg Phe Asn His Asn Leu Arg Lys Glu Leu Gly Ile His Lys
    50                  55                  60

Cys Phe Leu Asn Phe Arg Ile Trp Thr Thr Leu Arg Pro Gln Thr Gly
65                  70                  75                  80
```

-continued

```
Leu Phe Leu Arg Val Phe Arg Tyr Gln Val Leu Lys Tyr Leu Asp Asn
                 85                  90                  95

Ile Gly Val Ile Ser Ile Asn Asp Val Ile Arg Ala Ala Cys His Val
            100                 105                 110

Leu Phe Asn Val Ile Glu Lys Thr Ile Glu Cys Gln Leu Thr His Glu
        115                 120                 125

Ile Lys Phe Asn Val Tyr
    130


<210> SEQ ID NO 9
<211> LENGTH: 132
<212> TYPE: PRT
<213> ORGANISM: Abutilon mosaic virus

<400> SEQUENCE: 9

Met Asp Ser Arg Thr Gly Glu Phe Ile Thr Val His Gln Ala Glu Asn
  1               5                  10                  15

Gly Val Tyr Ile Trp Glu Ile Ala Asn Pro Leu Tyr Phe Arg Ile Tyr
             20                  25                  30

Lys Val Glu Asp Pro Leu Tyr Thr Arg Thr Arg Ile Tyr His Val Gln
         35                  40                  45

Ile Arg Phe Asn His Asn Leu Arg Arg Ala Leu His Leu His Lys Ala
     50                  55                  60

Tyr Leu Asn Phe Gln Val Trp Thr Thr Ser Met Thr Ala Ser Gly Ser
 65                  70                  75                  80

Ile Tyr Leu Asn Arg Phe Arg Arg Leu Val Asn Met Tyr Leu Asp Gln
                 85                  90                  95

Leu Gly Val Ile Ser Ile Asn Asn Val Ile Arg Ala Val Gln Phe Ala
            100                 105                 110

Thr Asn Arg Thr Tyr Val Asn Tyr Val Leu Glu Asn His Ser Ile Lys
        115                 120                 125

Phe Lys Phe Tyr
    130


<210> SEQ ID NO 10
<211> LENGTH: 132
<212> TYPE: PRT
<213> ORGANISM: Bean dwarf mosaic virus

<400> SEQUENCE: 10

Met Asp Ser Arg Thr Gly Glu Leu Ile Thr Ala Leu Gln Ala Glu Asn
  1               5                  10                  15
Gly Val Tyr Ile Trp Glu Ile Glu Asn Pro Leu Tyr Phe Lys Ile Tyr
             20                  25                  30
Arg Val Glu Glu Pro Leu Tyr Thr Asn Ser Arg Val Tyr Ser Val Gln
         35                  40                  45
Ile Arg Phe Asn His Asn Leu Arg Arg Ala Leu His Leu His Lys Ala
     50                  55                  60
Phe Leu Asn Phe Gln Val Trp Thr Ile Ser Thr Thr Ala Ser Gly Ser
 65                  70                  75                  80
Thr Tyr Leu Asn Arg Phe Lys His Leu Val Ile Met Tyr Leu Asp Gln
                 85                  90                  95
Leu Gly Ile Ile Ser Ile Asn Asn Val Ile Arg Gly Val Arg Phe Ala
            100                 105                 110
Thr Asp Arg Ser Tyr Val Thr His Val Ile Glu Tyr His Ser Ile Lys
        115                 120                 125
Phe Lys Leu Tyr
    130


<210> SEQ ID NO 11
<211> LENGTH: 132
<212> TYPE: PRT
<213> ORGANISM: Bean golden mosaic virus
```

-continued

<400> SEQUENCE: 11

Met Asp Ser Arg Thr Gly Glu Asn Ile Thr Ala His Gln Ala Glu Asn
1 5 10 15

Ser Val Phe Ile Trp Glu Val Pro Asn Pro Leu Tyr Phe Lys Ile Met
20 25 30

Arg Val Glu Asp Pro Ala Tyr Thr Arg Thr Arg Ile Tyr His Ile Gln
35 40 45

Ile Arg Phe Asn His Asn Leu Arg Lys Ala Leu Asp Leu His Lys Ala
50 55 60

Phe Leu Asn Phe Gln Val Trp Thr Thr Ser Ile Gln Ala Ser Gly Thr
65 70 75 80

Thr Tyr Leu Asn Arg Phe Arg Leu Leu Val Leu Leu Tyr Leu His Arg
85 90 95

Leu Gly Val Ile Gly Ile Asn Asn Val Ile Arg Ala Val Gln Phe Ala
100 105 110

Thr Asn Lys Ser Tyr Val Asn Thr Val Leu Glu Asn His Asp Ile Lys
115 120 125

Tyr Lys Phe Tyr
130

<210> SEQ ID NO 12
<211> LENGTH: 132
<212> TYPE: PRT
<213> ORGANISM: BGMV-Brazilian isolate

<400> SEQUENCE: 12

Met Asp Ser Arg Thr Gly Glu Arg Ile Thr Ala Arg Gln Ala Glu Asn
1 5 10 15

Gly Val Tyr Ile Trp Glu Ile Ser Asn Pro Leu Tyr Phe Lys Met Tyr
20 25 30

Asn Val Glu Asp Leu Gln Tyr Thr Thr Thr Arg Val Tyr His Leu Gln
35 40 45

Ile Arg Phe Asn His Asn Leu Arg Asn Lys Leu Gly Leu His Lys Ala
50 55 60

Phe Leu Asn Phe Gln Val Trp Thr Ile Ser Leu Gln Ala Ser Gly Thr
65 70 75 80

Thr Tyr Leu Asn Arg Phe Lys Tyr Leu Val Leu Leu Tyr Leu Asp Arg
85 90 95

Ile Gly Val Ile Ser Leu Asn Asn Val Ile Arg Ala Val Arg Phe Ala
100 105 110

Thr Asp Lys Ser Tyr Val Asn Tyr Val Leu Glu Asn His Glu Ile Lys
115 120 125

Tyr Lys Phe Tyr
130

<210> SEQ ID NO 13
<211> LENGTH: 132
<212> TYPE: PRT
<213> ORGANISM: Pepper huasteco virus

<400> SEQUENCE: 13

Met Asp Leu Arg Thr Gly Val Pro Ile Thr Ala Ala Gln Ala Ala Asn
1 5 10 15

Gly Val Phe Ile Trp Glu Leu Arg Asn Pro Leu Tyr Phe Lys Ile Arg
20 25 30

-continued

```
Leu Val Glu Thr Pro Met Tyr Thr Arg Ser Arg Val Phe His Ile Gln
        35                  40                  45

Val Arg Ala Asn His Asn Met Arg Thr Ala Leu Gly Leu His Lys Ala
    50                  55                  60

Tyr Phe Asn Phe Gln Val Trp Thr Thr Leu Thr Thr Ile Ser Gly Gln
65                  70                  75                  80

Ile Tyr Leu Asn Arg Phe Lys Leu Leu Val Met Phe Tyr Leu Asp Asn
                85                  90                  95

Leu Gly Leu Ile Ser Val Asn Asn Val Ile Arg Ala Val Ser Phe Ala
            100                 105                 110

Thr Asp Lys Arg Tyr Val Asn Ala Val Leu Glu Asn His Glu Ile Ile
        115                 120                 125

Tyr Lys Leu Tyr
    130


<210> SEQ ID NO 14
<211> LENGTH: 132
<212> TYPE: PRT
<213> ORGANISM: Potato yellow mosaic virus

<400> SEQUENCE: 14

Met Asp Ser Arg Thr Gly Glu Leu Ile Thr Ala Arg Gln Ala Glu Asn
  1               5                  10                  15

Gly Val Phe Ile Trp Glu Ile Glu Asn Pro Leu Tyr Phe Lys Ile Asn
            20                  25                  30

Gln Val Glu Asp Met Gln Tyr Thr Arg Thr Arg Ile Tyr Ser Val Gln
        35                  40                  45

Ile Arg Phe Asn His Asn Leu Arg Arg Ala Leu Asp Leu His Lys Ala
    50                  55                  60

Tyr Leu Asn Phe Gln Val Trp Thr Thr Ser Met Thr Ala Ser Gly Ser
65                  70                  75                  80

Asn Tyr Leu Ala Arg Phe Arg Gln Leu Val Leu Leu Tyr Leu Asp Arg
                85                  90                  95

Leu Gly Val Ile Ser Ile Asn Asn Val Ile Arg Ser Val Arg Phe Ala
            100                 105                 110

Thr Asp Arg Ser Tyr Val Asn Tyr Val Leu Glu Asn His Ser Ile Lys
        115                 120                 125

Tyr Lys Phe Tyr
    130


<210> SEQ ID NO 15
<211> LENGTH: 134
<212> TYPE: PRT
<213> ORGANISM: Squash leaf curl virus

<400> SEQUENCE: 15

Met Val Met Asp Leu Arg Thr Trp Asp Asp Ile Thr Val His Gln Ala
  1               5                  10                  15

Glu Asn Ser Val Phe Ile Trp Glu Val Pro Asn Pro Leu Tyr Phe Lys
            20                  25                  30

Met Tyr Xaa Val Glu Asp Pro Leu Tyr Thr His Thr Arg Ile Tyr His
        35                  40                  45

Ile Gln Ile Arg Phe Asn His Asn Leu Arg Arg Ala Leu Asn Leu His
    50                  55                  60

Lys Ala Phe Leu Asn Phe Gln Val Trp Thr Glu Ser Ile Arg Ala Ser
65                  70                  75                  80
```

-continued

```
Gly Thr Thr Tyr Leu Asn Arg Phe Arg His Leu Val Met Leu Tyr Leu
                 85                  90                  95

Asp Arg Leu Gly Val Ile Gly Leu Asn Asn Val Ile Arg Ala Val Ser
            100                 105                 110

Trp Ala Thr Asp Arg Ser Tyr Val Asn Tyr Val Leu Glu Asn His Glu
        115                 120                 125

Ile Lys Phe Lys Ile Tyr
    130


<210> SEQ ID NO 16
<211> LENGTH: 132
<212> TYPE: PRT
<213> ORGANISM: Tomato golden mosaic virus

<400> SEQUENCE: 16

Met Asp Ser Arg Thr Gly Glu Pro Ile Thr Val Pro Gln Ala Glu Asn
  1               5                  10                  15

Gly Val Tyr Ile Trp Glu Ile Thr Asn Pro Leu Tyr Phe Lys Ile Ile
             20                  25                  30

Ser Val Glu Asp Pro Leu Tyr Thr Asn Thr Arg Ile Tyr His Leu Gln
         35                  40                  45

Ile Arg Phe Asn His Asn Leu Arg Arg Ala Leu Asp Leu His Lys Ala
     50                  55                  60

Phe Leu Asn Phe Gln Val Trp Thr Thr Ser Thr Thr Ala Ser Gly Arg
 65                  70                  75                  80

Thr Tyr Leu Asn Arg Phe Lys Tyr Leu Val Met Leu Tyr Leu Glu Gln
                 85                  90                  95

Leu Gly Val Ile Cys Ile Asn Asn Val Ile Arg Ala Val Arg Phe Ala
            100                 105                 110

Thr Asp Arg Ser Tyr Ile Thr His Val Leu Glu Asn His Ser Ile Lys
        115                 120                 125

Tyr Lys Phe Tyr
    130


<210> SEQ ID NO 17
<211> LENGTH: 132
<212> TYPE: PRT
<213> ORGANISM: Tomato mottle virus

<400> SEQUENCE: 17

Met Asp Ser Arg Thr Gly Glu Leu Ile Thr Ala His Gln Ala Glu Asn
  1               5                  10                  15

Gly Val Tyr Ile Trp Glu Leu Glu Asn Pro Leu Tyr Phe Lys Ile His
             20                  25                  30

Arg Val Glu Asp Pro Leu Tyr Thr Arg Thr Arg Val Tyr His Val Gln
         35                  40                  45

Ile Arg Phe Asn His Asn Leu Arg Lys Ala Leu His Leu His Lys Ala
     50                  55                  60

Tyr Leu Asn Phe Gln Val Trp Thr Thr Ser Met Thr Ala Ser Gly Ser
 65                  70                  75                  80

Ile Tyr Leu Ala Arg Phe Arg Tyr Leu Val Asn Met Tyr Leu Asp Gln
                 85                  90                  95

Leu Gly Val Ile Ser Ile Asn Asn Val Val Arg Ala Val Arg Phe Ala
            100                 105                 110

Thr Asn Arg Val Tyr Val Asn His Val Leu Glu Asn His Ser Ile Lys
        115                 120                 125
```

-continued

```
Phe Lys Phe Tyr
    130


<210> SEQ ID NO 18
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#15)

<400> SEQUENCE: 18

Met Ala Ser Ala Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 19
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#17)

<400> SEQUENCE: 19

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Ala Ala Ala Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130
```

-continued

<210> SEQ ID NO 20
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#19)

<400> SEQUENCE: 20

```
Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Ala Ala Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130
```

<210> SEQ ID NO 21
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#21)

<400> SEQUENCE: 21

```
Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Ala Ala Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130
```

<210> SEQ ID NO 22
<211> LENGTH: 130

-continued

<212> TYPE: PRT
<213> ORGANISM: Artificial Sequence
<220> FEATURE:
<223> OTHER INFORMATION: Description of Artificial Sequence: TYCLV mutant C3 (mC3#23)

<400> SEQUENCE: 22

Met Asp Ser Arg Thr Gly Glu Leu Ile Thr Ala Pro Gln Ala Glu Asn
1 5 10 15

Gly Val Phe Ile Trp Glu Ile Asn Asn Pro Leu Tyr Phe Lys Ile Thr
20 25 30

Asp His Ser Gln Arg Pro Phe Leu Met Asn His Asp Ile Ile Ser Ile
35 40 45

Gln Ile Arg Phe Asn His Asn Ile Arg Lys Val Met Gly Ile His Lys
50 55 60

Cys Phe Leu Asn Phe Arg Ile Trp Thr Gln Thr Gly Arg Phe Leu Arg
65 70 75 80

Val Ala Ala Tyr Gly Val Leu Lys Tyr Leu Asp Ser Leu Gly Val Ile
85 90 95

Ser Ile Asn Asn Val Ile Arg Ala Val Asp His Val Leu Tyr Asp Val
100 105 110

Leu Glu Asn Thr Ile Asn Val Thr Glu Thr His Asp Ile Lys Tyr Lys
115 120 125

Phe Tyr
130

<210> SEQ ID NO 23
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#25)

<400> SEQUENCE: 23

Met Asp Ser Arg Thr Gly Glu Leu Ile Thr Ala Pro Gln Ala Glu Asn
1 5 10 15

Gly Val Phe Ile Trp Glu Ile Asn Asn Pro Leu Tyr Phe Lys Ile Thr
20 25 30

Asp His Ser Gln Arg Pro Phe Leu Met Asn His Asp Ile Ile Ser Ile
35 40 45

Gln Ile Arg Phe Asn His Asn Ile Arg Lys Val Met Gly Ile His Lys
50 55 60

Cys Phe Leu Asn Phe Arg Ile Trp Thr Thr Gln Thr Gly Arg Phe Leu
65 70 75 80

Arg Val Phe Arg Tyr Gly Val Leu Lys Tyr Leu Asp Ser Leu Gly Val
85 90 95

Ile Ser Ile Ala Ala Val Ile Arg Ala Val Asp His Val Leu Tyr Asp
100 105 110

Val Leu Glu Asn Thr Ile Asn Val Thr Glu Thr His Asp Ile Lys Tyr
115 120 125

Lys Phe Tyr
130

<210> SEQ ID NO 24
<211> LENGTH: 131
<212> TYPE: PRT
<213> ORGANISM: Artificial Sequence
<220> FEATURE:

-continued

<223> OTHER INFORMATION: Description of Artificial Sequence: TYCLV
mutant C3 (mC3#27)

<400> SEQUENCE: 24

```
Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Ala Tyr
        115                 120                 125

Lys Phe Tyr
    130
```

<210> SEQ ID NO 25
<211> LENGTH: 131
<212> TYPE: PRT
<213> ORGANISM: Artificial Sequence
<220> FEATURE:
<223> OTHER INFORMATION: Description of Artificial Sequence: TYCLV
mutant C3 (mC3#29)

<400> SEQUENCE: 25

```
Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Ala
        115                 120                 125

Ala Phe Ala
    130
```

<210> SEQ ID NO 26
<211> LENGTH: 131
<212> TYPE: PRT
<213> ORGANISM: Artificial Sequence
<220> FEATURE:
<223> OTHER INFORMATION: Description of Artificial Sequence: TYCLV
mutant C3 (mC3#31)

-continued

```
<400> SEQUENCE: 26

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Ala Ala Thr Gln Thr Gly Arg Phe Leu
 65                  70                  75                  80

Arg Val Phe Ala Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 27
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#33)

<400> SEQUENCE: 27

Met Asp Ser Arg Thr Gly Ala Leu Ile Ala Ala Pro Ala Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 28
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#35)

<400> SEQUENCE: 28

Met Asp Ser Arg Thr Gly Glu Leu Ile Thr Ala Pro Gln Ala Glu Asn
```

-continued 1 5 10 15

Gly Val Ala Ile Ala Glu Ile Asn Asn Pro Leu Tyr Phe Lys Ile Thr
20 25 30

Asp His Ser Gln Arg Pro Phe Leu Met Asn His Asp Ile Ile Ser Ile
35 40 45

Gln Ile Arg Phe Asn His Asn Ile Arg Lys Val Met Gly Ile His Lys
50 55 60

Cys Phe Leu Asn Phe Arg Ile Trp Thr Thr Gln Thr Gly Arg Phe Leu
65 70 75 80

Arg Val Phe Arg Tyr Gly Val Leu Lys Tyr Leu Asp Ser Leu Gly Val
85 90 95

Ile Ser Ile Asn Asn Val Ile Arg Ala Val Asp His Val Leu Tyr Asp
100 105 110

Val Leu Glu Asn Thr Ile Asn Val Thr Glu Thr His Asp Ile Lys Tyr
115 120 125

Lys Phe Tyr
130

<210> SEQ ID NO 29
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#37)

<400> SEQUENCE: 29

Met Asp Ser Arg Thr Gly Glu Leu Ile Thr Ala Pro Gln Ala Glu Asn
1 5 10 15

Gly Val Phe Ile Trp Glu Ile Asn Asn Pro Leu Tyr Phe Lys Ile Thr
20 25 30

Asp His Ser Gln Ala Ala Ala Leu Met Asn His Asp Ile Ile Ser Ile
35 40 45

Gln Ile Arg Phe Asn His Asn Ile Arg Lys Val Met Gly Ile His Lys
50 55 60

Cys Phe Leu Asn Phe Arg Ile Trp Thr Thr Gln Thr Gly Arg Phe Leu
65 70 75 80

Arg Val Phe Arg Tyr Gly Val Leu Lys Tyr Leu Asp Ser Leu Gly Val
85 90 95

Ile Ser Ile Asn Asn Val Ile Arg Ala Val Asp His Val Leu Tyr Asp
100 105 110

Val Leu Glu Asn Thr Ile Asn Val Thr Glu Thr His Asp Ile Lys Tyr
115 120 125

Lys Phe Tyr
130

<210> SEQ ID NO 30
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#39)

<400> SEQUENCE: 30

Met Asp Ser Arg Thr Gly Glu Leu Ile Thr Ala Pro Gln Ala Glu Asn
1 5 10 15

Gly Val Phe Ile Trp Glu Ile Asn Asn Pro Leu Tyr Phe Lys Ile Thr

-continued

```
            20                  25                  30

Asp His Ser Gln Arg Pro Phe Leu Met Asn His Asp Ile Ile Ser Ile
        35                  40                  45

Ala Ile Ala Ala Asn His Asn Ile Arg Lys Val Met Gly Ile His Lys
    50                  55                  60

Cys Phe Leu Asn Phe Arg Ile Trp Thr Thr Gln Thr Gly Arg Phe Leu
65                  70                  75                  80

Arg Val Phe Arg Tyr Gly Val Leu Lys Tyr Leu Asp Ser Leu Gly Val
                85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130
```

<210> SEQ ID NO 31
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#41)

<400> SEQUENCE: 31

```
Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
            20                  25                  30

Asp His Ser Gln Arg Pro Phe Leu Met Asn His Asp Ile Ile Ser Ile
        35                  40                  45

Gln Ile Arg Phe Ala Ala Ala Ile Arg Lys Val Met Gly Ile His Lys
    50                  55                  60

Cys Phe Leu Asn Phe Arg Ile Trp Thr Thr Gln Thr Gly Arg Phe Leu
65                  70                  75                  80

Arg Val Phe Arg Tyr Gly Val Leu Lys Tyr Leu Asp Ser Leu Gly Val
                85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130
```

<210> SEQ ID NO 32
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#43)

<400> SEQUENCE: 32

```
Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
            20                  25                  30

Asp His Ser Gln Arg Pro Phe Leu Met Asn His Asp Ile Ile Ser Ile
```

-continued

```
        35                  40                  45

Gln Ile Arg Phe Asn His Asn Ile Arg Lys Val Met Gly Ile Ala Ala
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 33
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#45)

<400> SEQUENCE: 33

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
            20                  25                  30

Asp His Ser Gln Arg Pro Phe Leu Met Asn His Asp Ile Ile Ser Ile
        35                  40                  45

Gln Ile Arg Phe Asn His Asn Ile Arg Lys Val Met Gly Ile His Lys
     50                  55                  60

Cys Ala Leu Ala Ala Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 34
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#47)

<400> SEQUENCE: 34

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
            20                  25                  30

Asp His Ser Gln Arg Pro Phe Leu Met Asn His Asp Ile Ile Ser Ile
        35                  40                  45

Gln Ile Arg Phe Asn His Asn Ile Arg Lys Val Met Gly Ile His Lys
```

-continued

```
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Ala Ala Leu Ala Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 35
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#49)

<400> SEQUENCE: 35

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Ala Ala Ala Ala Ile Lys Tyr
        115                 120                 125

Lys Phe Tyr
    130


<210> SEQ ID NO 36
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#51)

<400> SEQUENCE: 36

Met Asp Ser Glu Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
```

-continued

```
65                  70                  75                  80

Arg Val Phe Arg Tyr Glu Val Leu Lys Tyr Leu Asp Ser Leu Gly Val
                85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 37
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#53)

<400> SEQUENCE: 37

Met Asp Ser Arg Thr Gly Lys Leu Ile Thr Ala Pro Gln Ala Glu Asn
  1               5                  10                  15

Gly Val Phe Ile Trp Glu Ile Asn Asn Pro Leu Tyr Phe Lys Ile Thr
            20                  25                  30

Asp His Ser Gln Arg Pro Phe Leu Met Asn His Asp Ile Ile Ser Ile
        35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 38
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#55)

<400> SEQUENCE: 38

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
            20                  25                  30

Asp His Ser Gln Arg Pro Phe Leu Met Asn His Asp Ile Ile Ser Ile
        35                  40                  45

Gln Ile Glu Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
```

-continued

```
                85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 39
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#57)

<400> SEQUENCE: 39

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
            20                  25                  30

Asp His Ser Gln Arg Pro Phe Leu Met Asn His Asp Ile Ile Ser Ile
        35                  40                  45

Gln Ile Arg Phe Asn His Asn Ile Glu Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 40
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#59)

<400> SEQUENCE: 40

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
            20                  25                  30

Asp His Ser Gln Arg Pro Phe Leu Met Asn His Asp Ile Ile Ser Ile
        35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Glu Val Phe Arg Tyr Gly Val Leu Lys Tyr Leu Asp Ser Leu Gly Val
                85                  90                  95

Ile Ser Ile Asn Asn Val Ile Arg Ala Val Asp His Val Leu Tyr Asp
```

-continued 100 105 110

Val Leu Glu Asn Thr Ile Asn Val Thr Glu Thr His Asp Ile Lys Tyr
115 120 125

Lys Phe Tyr
130

<210> SEQ ID NO 41
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#61)

<400> SEQUENCE: 41

Met Asp Ser Arg Thr Gly Glu Leu Ile Thr Ala Pro Gln Ala Glu Asn
1 5 10 15

Gly Val Phe Ile Trp Glu Ile Asn Asn Pro Leu Tyr Phe Lys Ile Thr
20 25 30

Asp His Ser Gln Arg Pro Phe Leu Met Asn His Asp Ile Ile Ser Ile
35 40 45

Gln Ile Arg Phe Asn His Asn Ile Arg Lys Val Met Gly Ile His Lys
50 55 60

Cys Phe Leu Asn Phe Arg Ile Trp Thr Thr Gln Thr Gly Arg Phe Leu
65 70 75 80

Arg Val Phe Arg Tyr Gly Val Leu Lys Tyr Leu Asp Ser Leu Gly Val
85 90 95

Ile Ser Ile Asn Asn Val Ile Glu Ala Val Asp His Val Leu Tyr Asp
100 105 110

Val Leu Glu Asn Thr Ile Asn Val Thr Glu Thr His Asp Ile Lys Tyr
115 120 125

Lys Phe Tyr
130

<210> SEQ ID NO 42
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#63)

<400> SEQUENCE: 42

Met Asp Ser Arg Thr Gly Glu Leu Ile Thr Ala Pro Gln Ala Glu Asn
1 5 10 15

Gly Val Phe Ile Trp Glu Ile Asn Asn Pro Leu Tyr Phe Lys Ile Thr
20 25 30

Asp His Ser Gln Arg Pro Phe Leu Met Asn His Asp Ile Ile Ser Ile
35 40 45

Gln Ile Arg Phe Asn His Asn Ile Arg Lys Val Met Gly Ile His Lys
50 55 60

Cys Phe Leu Asn Phe Arg Ile Trp Thr Thr Gln Thr Gly Arg Phe Leu
65 70 75 80

Arg Val Phe Arg Tyr Gly Val Leu Lys Tyr Leu Asp Ser Leu Gly Val
85 90 95

Ile Ser Ile Asn Asn Val Ile Arg Ala Val Asp His Val Leu Tyr Asp
100 105 110

Val Leu Glu Asn Thr Ile Asn Val Thr Glu Thr His Lys Ile Lys Tyr

-continued

```
        115                 120                 125

Lys Phe Tyr
    130


<210> SEQ ID NO 43
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#65)

<400> SEQUENCE: 43

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Glu Tyr
        115                 120                 125

Lys Phe Tyr
    130


<210> SEQ ID NO 44
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#67)

<400> SEQUENCE: 44

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Ala Ala Ala Ala Ala Ala Ala Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
```

-continued

```
    130


<210> SEQ ID NO 45
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#69)

<400> SEQUENCE: 45

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Ala Leu Ala Ala Arg Ile Ala Ala Thr Gln Thr Gly Arg Phe Leu
 65                  70                  75                  80

Arg Val Phe Arg Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130


<210> SEQ ID NO 46
<211> LENGTH: 131
<212> TYPE: PRT
<213> ORGANISM: Artificial Sequence
<220> FEATURE:
<223> OTHER INFORMATION: Description of Artificial Sequence: TYCLV
      mutant C3 (mC3#71)

<400> SEQUENCE: 46

Met Asp Ser Arg Thr Gly Glu Leu Ile Thr Ala Pro Gln Ala Glu Asn
  1               5                  10                  15

Gly Val Phe Ile Trp Glu Ile Asn Asn Pro Leu Tyr Phe Lys Ile Thr
             20                  25                  30

Asp His Ser Gln Arg Pro Phe Leu Met Asn His Asp Ile Ile Ser Ile
         35                  40                  45

Gln Ile Arg Phe Asn His Asn Ile Arg Lys Val Met Gly Ile His Lys
     50                  55                  60

Cys Phe Leu Asn Phe Arg Ile Trp Thr Thr Gln Thr Gly Arg Phe Leu
 65                  70                  75                  80

Ala Ala Ala Ala Tyr Gly Val Leu Lys Tyr Leu Asp Ser Leu Gly Val
                 85                  90                  95

Ile Ser Ile Asn Asn Val Ile Arg Ala Val Asp His Val Leu Tyr Asp
            100                 105                 110

Val Leu Glu Asn Thr Ile Asn Val Thr Glu Thr His Asp Ile Lys Tyr
        115                 120                 125

Lys Phe Tyr
    130
```

-continued

<210> SEQ ID NO 47
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#73)

<400> SEQUENCE: 47

Met Asp Ser Arg Thr Gly Glu Leu Ile Thr Ala Pro Gln Ala Glu Asn
1 5 10 15

Gly Val Phe Ile Trp Glu Ile Asn Asn Pro Leu Tyr Phe Lys Ile Thr
20 25 30

Asp His Ser Gln Arg Pro Phe Leu Met Asn His Asp Ile Ile Ser Ile
35 40 45

Gln Ile Arg Phe Asn His Asn Ile Arg Lys Val Met Gly Ile His Lys
50 55 60

Cys Phe Leu Asn Phe Arg Ile Trp Thr Thr Gln Thr Gly Arg Phe Leu
65 70 75 80

Arg Val Phe Arg Tyr Gly Ala Ala Ala Ala Ala Ala Ser Leu Gly Val
85 90 95

Ile Ser Ile Asn Asn Val Ile Arg Ala Val Asp His Val Leu Tyr Asp
100 105 110

Val Leu Glu Asn Thr Ile Asn Val Thr Glu Thr His Asp Ile Lys Tyr
115 120 125

Lys Phe Tyr
130

<210> SEQ ID NO 48
<211> LENGTH: 131
<212> TYPE: PRT
<213> ORGANISM: Artificial Sequence
<220> FEATURE:
<223> OTHER INFORMATION: Description of Artificial Sequence: TYCLV mutant C3 (mC3#75)

<400> SEQUENCE: 48

Met Asp Ser Arg Thr Gly Glu Leu Ile Thr Ala Pro Gln Ala Glu Asn
1 5 10 15

Gly Val Phe Ile Trp Glu Ile Asn Asn Pro Leu Tyr Phe Lys Ile Thr
20 25 30

Asp His Ser Gln Arg Pro Phe Leu Met Asn His Asp Ile Ile Ser Ile
35 40 45

Gln Ile Arg Phe Asn His Asn Ile Glu Glu Val Met Gly Ile His Lys
50 55 60

Cys Phe Leu Asn Phe Arg Ile Trp Thr Thr Gln Thr Gly Arg Phe Leu
65 70 75 80

Arg Val Phe Arg Tyr Gly Val Leu Lys Tyr Leu Asp Ser Leu Gly Val
85 90 95

Ile Ser Ile Asn Asn Val Ile Arg Ala Val Asp His Val Leu Tyr Asp
100 105 110

Val Leu Glu Asn Thr Ile Asn Val Thr Glu Thr His Asp Ile Lys Tyr
115 120 125

Lys Phe Tyr
130

<210> SEQ ID NO 49
<211> LENGTH: 132
<212> TYPE: PRT

-continued

<213> ORGANISM: Artificial Sequence
<220> FEATURE:
<223> OTHER INFORMATION: Description of Artificial Sequence: TGMV AL3 mutant (mAL3#67)

<400> SEQUENCE: 49

```
Met Asp Ser Arg Thr Gly Glu Pro Ile Thr Val Pro Gln Ala Glu Asn
  1               5                  10                  15

Gly Val Tyr Ile Trp Glu Ile Thr Asn Pro Leu Tyr Phe Lys Ile Ile
             20                  25                  30

Ser Val Glu Asp Pro Leu Tyr Thr Asn Thr Arg Ile Tyr His Leu Ala
         35                  40                  45

Ala Ala Ala Ala Ala Ala Leu Arg Arg Ala Leu Asp Leu His Lys Ala
     50                  55                  60

Phe Leu Asn Phe Gln Val Trp Thr Thr Ser Thr Thr Ala Ser Gly Arg
 65                  70                  75                  80

Thr Tyr Leu Asn Arg Phe Lys Tyr Leu Val Met Leu Tyr Leu Glu Gln
                 85                  90                  95

Leu Gly Val Ile Cys Ile Asn Asn Val Ile Arg Ala Val Arg Phe Ala
            100                 105                 110

Thr Asp Arg Ser Tyr Ile Thr His Val Leu Glu Asn His Ser Ile Lys
        115                 120                 125

Tyr Lys Phe Tyr
    130
```

<210> SEQ ID NO 50
<211> LENGTH: 132
<212> TYPE: PRT
<213> ORGANISM: Artificial Sequence
<220> FEATURE:
<223> OTHER INFORMATION: Description of Artificial Sequence: TGMV mutant AL3 (mAL3#69)

<400> SEQUENCE: 50

```
Met Asp Ser Arg Thr Gly Glu Pro Ile Thr Val Pro Gln Ala Glu Asn
  1               5                  10                  15

Gly Val Tyr Ile Trp Glu Ile Thr Asn Pro Leu Tyr Phe Lys Ile Ile
             20                  25                  30

Ser Val Glu Asp Pro Leu Tyr Thr Asn Thr Arg Ile Tyr His Leu Gln
         35                  40                  45

Ile Arg Phe Asn His Asn Leu Arg Arg Ala Leu Asp Leu His Lys Ala
     50                  55                  60

Ala Leu Ala Ala Gln Val Ala Ala Thr Ser Thr Thr Ala Ser Gly Arg
 65                  70                  75                  80

Thr Tyr Leu Asn Arg Phe Lys Tyr Leu Val Met Leu Tyr Leu Glu Gln
                 85                  90                  95

Leu Gly Val Ile Cys Ile Asn Asn Val Ile Arg Ala Val Arg Phe Ala
            100                 105                 110

Thr Asp Arg Ser Tyr Ile Thr His Val Leu Glu Asn His Ser Ile Lys
        115                 120                 125

Tyr Lys Phe Tyr
    130
```

<210> SEQ ID NO 51
<211> LENGTH: 132
<212> TYPE: PRT
<213> ORGANISM: Artificial Sequence
<220> FEATURE:
<223> OTHER INFORMATION: Description of Artificial Sequence: TGMV mutant -continued

```
      AL3 (mAL3#71)

<400> SEQUENCE: 51

Met Asp Ser Arg Thr Gly Glu Pro Ile Thr Val Pro Gln Ala Glu Asn
  1               5                  10                  15

Gly Val Tyr Ile Trp Glu Ile Thr Asn Pro Leu Tyr Phe Lys Ile Ile
             20                  25                  30

Ser Val Glu Asp Pro Leu Tyr Thr Asn Thr Arg Ile Tyr His Leu Gln
         35                  40                  45

Ile Arg Phe Asn His Asn Leu Arg Arg Ala Leu Asp Leu His Lys Ala
     50                  55                  60

Phe Leu Asn Phe Gln Val Trp Thr Thr Ser Thr Thr Ala Ser Gly Arg
 65                  70                  75                  80

Thr Tyr Leu Ala Ala Ala Ala Tyr Leu Val Met Leu Tyr Leu Glu Gln
                 85                  90                  95

Leu Gly Val Ile Cys Ile Asn Asn Val Ile Arg Ala Val Arg Phe Ala
            100                 105                 110

Thr Asp Arg Ser Tyr Ile Thr His Val Leu Glu Asn His Ser Ile Lys
        115                 120                 125

Tyr Lys Phe Tyr
    130


<210> SEQ ID NO 52
<211> LENGTH: 132
<212> TYPE: PRT
<213> ORGANISM: Artificial Sequence
<220> FEATURE:
<223> OTHER INFORMATION: Description of Artificial Sequence:TGMV mutant
      AL3 (mAL3#73)

<400> SEQUENCE: 52

Met Asp Ser Arg Thr Gly Glu Pro Ile Thr Val Pro Gln Ala Glu Asn
  1               5                  10                  15

Gly Val Tyr Ile Trp Glu Ile Thr Asn Pro Leu Tyr Phe Lys Ile Ile
             20                  25                  30

Ser Val Glu Asp Pro Leu Tyr Thr Asn Thr Arg Ile Tyr His Leu Gln
         35                  40                  45

Ile Arg Phe Asn His Asn Leu Arg Arg Ala Leu Asp Leu His Lys Ala
     50                  55                  60

Phe Leu Asn Phe Gln Val Trp Thr Thr Ser Thr Thr Ala Ser Gly Arg
 65                  70                  75                  80

Thr Tyr Leu Asn Arg Phe Lys Tyr Leu Ala Ala Ala Ala Ala Ala Gln
                 85                  90                  95

Leu Gly Val Ile Cys Ile Asn Asn Val Ile Arg Ala Val Arg Phe Ala
            100                 105                 110

Thr Asp Arg Ser Tyr Ile Thr His Val Leu Glu Asn His Ser Ile Lys
        115                 120                 125

Tyr Lys Phe Tyr
    130


<210> SEQ ID NO 53
<211> LENGTH: 132
<212> TYPE: PRT
<213> ORGANISM: Artificial Sequence
<220> FEATURE:
<223> OTHER INFORMATION: Description of Artificial Sequence:TGMV mutant
      AL3 (mAL3#75)

<400> SEQUENCE: 53
```

-continued

```
Met Asp Ser Arg Thr Gly Glu Pro Ile Thr Val Pro Gln Ala Glu Asn
  1               5                  10                  15

Gly Val Tyr Ile Trp Glu Ile Thr Asn Pro Leu Tyr Phe Lys Ile Ile
             20                  25                  30

Ser Val Glu Asp Pro Leu Tyr Thr Asn Thr Arg Ile Tyr His Leu Gln
         35                  40                  45

Ile Arg Phe Asn His Asn Leu Glu Glu Ala Leu Asp Leu His Lys Ala
     50                  55                  60

Phe Leu Asn Phe Gln Val Trp Thr Thr Ser Thr Thr Ala Ser Gly Arg
 65                  70                  75                  80

Thr Tyr Leu Asn Arg Phe Lys Tyr Leu Val Met Leu Tyr Leu Glu Gln
                 85                  90                  95

Leu Gly Val Ile Cys Ile Asn Asn Val Ile Arg Ala Val Arg Phe Ala
            100                 105                 110

Thr Asp Arg Ser Tyr Ile Thr His Val Leu Glu Asn His Ser Ile Lys
        115                 120                 125

Tyr Lys Phe Tyr
    130


<210> SEQ ID NO 54
<211> LENGTH: 132
<212> TYPE: PRT
<213> ORGANISM: Artificial Sequence
<220> FEATURE:
<223> OTHER INFORMATION: Description of Artificial Sequence:TGMV mutant
      AL3 (mAL3#17)

<400> SEQUENCE: 54

Met Asp Ser Arg Thr Gly Glu Pro Ile Thr Val Pro Gln Ala Glu Asn
  1               5                  10                  15

Gly Val Tyr Ile Trp Glu Ile Thr Asn Pro Leu Ala Ala Ala Ile Ile
             20                  25                  30

Ser Val Glu Asp Pro Leu Tyr Thr Asn Thr Arg Ile Tyr His Leu Gln
         35                  40                  45

Ile Arg Phe Asn His Asn Leu Arg Arg Ala Leu Asp Leu His Lys Ala
     50                  55                  60

Phe Leu Asn Phe Gln Val Trp Thr Thr Ser Thr Thr Ala Ser Gly Arg
 65                  70                  75                  80

Thr Tyr Leu Asn Arg Phe Lys Tyr Leu Val Met Leu Tyr Leu Glu Gln
                 85                  90                  95

Leu Gly Val Ile Cys Ile Asn Asn Val Ile Arg Ala Val Arg Phe Ala
            100                 105                 110

Thr Asp Arg Ser Tyr Ile Thr His Val Leu Glu Asn His Ser Ile Lys
        115                 120                 125

Tyr Lys Phe Tyr
    130
```